(12) United States Patent
Deisseroth et al.

(10) Patent No.: US 9,693,692 B2
(45) Date of Patent: *Jul. 4, 2017

(54) SYSTEM, METHOD AND APPLICATIONS INVOLVING IDENTIFICATION OF BIOLOGICAL CIRCUITS SUCH AS NEUROLOGICAL CHARACTERISTICS

(71) Applicant: The Board of Trustees of the Leland Stanford Junior University, Palo Alto, CA (US)

(72) Inventors: Karl Deisseroth, Palo Alto, CA (US); Raag D. Airan, Menlo Park, CA (US); Leslie A. Meltzer, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1015 days.

This patent is subject to a terminal disclaimer.

(21) Appl. No.: 13/763,132

(22) Filed: Feb. 8, 2013

(65) Prior Publication Data

US 2013/0284920 A1  Oct. 31, 2013

Related U.S. Application Data

(63) Continuation of application No. 12/031,651, filed on Feb. 14, 2008, now Pat. No. 8,401,609.

(Continued)

(51) Int. Cl.
*A61B 5/00* (2006.01)
*G01N 21/21* (2006.01)
*G01N 21/64* (2006.01)

(52) U.S. Cl.
CPC ........... *A61B 5/0059* (2013.01); *G01N 21/21* (2013.01); *A61B 5/4848* (2013.01);

(Continued)

(58) Field of Classification Search
CPC .... A61B 5/4848; A61B 5/0059; G01N 21/21; G01N 21/6452; G01N 2021/217; G01N 2021/218

See application file for complete search history.

(56) References Cited

U.S. PATENT DOCUMENTS 2,968,302 A  1/1961  Fry et al.
3,131,690 A  5/1964  Innis et al.

(Continued)

FOREIGN PATENT DOCUMENTS

CN  1079464 A  12/1993
EP  1 334 748  8/2003

(Continued)

OTHER PUBLICATIONS

Petersen et al. "Functionally Independent Columns of Rat Somatosensory Barrel Cortex Revealed with Voltage-Sensitive Dye Imaging." J of Neuroscience, Nov. 1, 2011, 21(21):8435-8446.*

(Continued)

*Primary Examiner* — Long V Le
*Assistant Examiner* — Angela M Hoffa
(74) *Attorney, Agent, or Firm* — Bozicevic, Field & Francis LLP; Paula A. Borden

(57) ABSTRACT

Various aspects are directed to systems and methods for assessing neural activity of a neural region having multiple subfields. In certain embodiments, a method includes evoking a cellular electrical response in at least one subfield due to neural activity in the neural region, capturing image data of the electrical response at a level sufficiently detailed in space and time to differentiate between polarization-based events of two respective portions of the subfield, and then assessing neural activity by correlating space and time information, from the captured data, for the two respective portions of the sub-field. Other more specific aspects of the (Continued)

invention involve different preparation and neural stimulation approaches which can vary depending on the application.

23 Claims, 18 Drawing Sheets

Related U.S. Application Data

(60) Provisional application No. 60/901,178, filed on Feb. 14, 2007.

(52) U.S. Cl.
CPC ... *G01N 21/6452* (2013.01); *G01N 2021/217* (2013.01); *G01N 2021/218* (2013.01)

(56) References Cited

U.S. PATENT DOCUMENTS

| | | |
|---|---|---|
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,696,722 B2 | 4/2014 | Deisseroth et al. |
| 8,815,582 B2 | 8/2014 | Deisseroth et al. |
| 8,906,360 B2 | 12/2014 | Deisseroth et al. |
| 8,926,959 B2 | 1/2015 | Deisseroth et al. |
| 9,057,734 B2 | 6/2015 | Cohen |
| 9,249,234 B2 | 2/2016 | Deisseroth et al. |
| 9,359,449 B2 | 6/2016 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0088060 A1 | 5/2003 | Benjamin et al. |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarakis et al. |
| 2004/0122475 A1 | 6/2004 | Myrick et al. |

(56) References Cited

U.S. PATENT DOCUMENTS

| | | |
|---|---|---|
| 2004/0203152 A1 | 10/2004 | Calos |
| 2004/0267118 A1 | 12/2004 | Dawson |
| 2005/0058987 A1 | 3/2005 | Shi et al. |
| 2005/0088177 A1 | 4/2005 | Schreck et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | deCharms |
| 2006/0161227 A1 | 7/2006 | Walsh et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Iyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand et al. |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0103551 A1 | 5/2008 | Masoud |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Aravanis et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0319008 A1 | 12/2009 | Mayer |
| 2009/0326603 A1 | 12/2009 | Boggs |
| 2010/0009444 A1 | 1/2010 | Herlitze et al. |
| 2010/0016783 A1 | 1/2010 | Bourke et al. |
| 2010/0145418 A1 | 6/2010 | Zhang et al. |
| 2010/0146645 A1 | 6/2010 | Vasar et al. |
| 2010/0190229 A1 | 7/2010 | Deisseroth et al. |
| 2010/0234273 A1 | 9/2010 | Deisseroth et al. |
| 2011/0021970 A1 | 1/2011 | Vo-Dinh et al. |
| 2011/0092800 A1 | 4/2011 | Yoo et al. |
| 2011/0105998 A1 | 5/2011 | Zhang et al. |
| 2011/0112179 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Deisseroth et al. |
| 2011/0172653 A1 | 7/2011 | Deisseroth et al. |
| 2011/0233046 A1 | 9/2011 | Nikolenko et al. |
| 2011/0301529 A1 | 12/2011 | Deisseroth et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0165904 A1 | 6/2012 | Deisseroth et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0144359 A1 | 6/2013 | Kishawi et al. |
| 2013/0286181 A1 | 10/2013 | Betzig et al. |
| 2015/0112411 A1 | 4/2015 | Beckman et al. |

FOREIGN PATENT DOCUMENTS

| | | |
|---|---|---|
| EP | 1873566 | 1/2008 |
| JP | 2006-295350 | 10/1994 |
| JP | 2004534508 | 11/2004 |
| JP | 2005034073 A | 2/2005 |
| JP | 2010227537 A | 10/2010 |
| JP | 2012508581 | 4/2012 |
| WO | WO 96/32076 | 10/1996 |
| WO | WO 00/27293 | 5/2000 |
| WO | WO 01-25466 | 4/2001 |
| WO | WO 03/106486 A2 | 2/2003 |
| WO | WO 2013/016486 | 2/2003 |
| WO | WO 03-040323 | 5/2003 |
| WO | WO 03/046141 | 6/2003 |
| WO | WO 03-084994 | 10/2003 |
| WO | WO 03-102156 | 12/2003 |
| WO | WO 2004/033647 | 4/2004 |
| WO | WO 2006/103678 | 10/2006 |
| WO | WO 2007-024391 | 3/2007 |
| WO | WO 2007-131180 | 11/2007 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO2009/119782 | 10/2009 |
| WO | WO 2009-131837 | 10/2009 |
| WO | WO 2009-0131837 | 10/2009 |
| WO | WO 2009/148946 | 12/2009 |
| WO | WO 2010/006049 | 1/2010 |
| WO | WO 2010/011404 A3 | 1/2010 |

(56) References Cited

FOREIGN PATENT DOCUMENTS

| WO | WO 2010/056970 | 5/2010 |
|---|---|---|
| WO | WO-2010123993 | 10/2010 |
| WO | WO 2011/005978 | 1/2011 |
| WO | WO 2011/066320 A3 | 6/2011 |
| WO | WO 2011/106783 | 9/2011 |
| WO | WO 2011-116238 A2 | 9/2011 |
| WO | WO 2011/127088 A3 | 10/2011 |
| WO | WO 2012/032103 | 3/2012 |
| WO | WO 2012/061676 | 5/2012 |
| WO | WO2012/061681 | 5/2012 |
| WO | WO2012/061684 | 5/2012 |
| WO | WO2012/061688 | 5/2012 |
| WO | WO2012/061690 | 5/2012 |
| WO | WO 2012/061741 | 5/2012 |
| WO | WO 2012/061744 | 5/2012 |
| WO | 2012/106407 | 8/2012 |
| WO | WO 2012/134704 A2 | 10/2012 |
| WO | WO 2013/003557 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2016/019075 | 2/2016 |

OTHER PUBLICATIONS

Zhang et al. "Channelrhodopsin-2 and optical control of excitable cells." Nature Methods, vol. 3, No. 10, Oct. 2006, pp. 785-492.*
Airan et al. "Integration of light-controlled neuronal firing and fast circuit imaging." Current Opinion in Neurobiology 2007, 17:587-592.*
Arenkiel, et al. "In vivo light-induced activation of neural circuitry in transgenic mice expressing Channelrhodopsin-2", Neuron, 2007, 54:205-218.
Milella et al. "Opposite roles of dopamine and orexin in quinpirole-induced excessive drinking: a rat model of psychotic polydipsia'" Psychopharmacology, 2010, 211:355-366.
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Xiong et al., "Interregional connectivity to primary motor cortex revealed using MRI resting state images", Hum Brain Mapp, 1999, 8(2-3):151-156.
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Bowers, et al.; "Genetic therapy for the nervous system"; Human Molecular Genetics; vol. 20, No. 1, pp. R28-R41 (2011).
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
GenBank Accession No. AC096118.6; Rattus norvegicus clone CH230-11 B15, 1-4, 24-25, Working Draft Sequence, 3 unordered pieces. May 10, 2003.
GenBank Accession No. U79717.1; Rattus norvegicus dopamine 02 receptor 1-4, 24-25 gene, promoter region and exon 1. Jan. 31, 1997.
Haim, et al.; "Gene Therapy to the Nervous System"; Stem Cell and Gene-Based Therapy; Section 2, pp. 133-154 (2006).
Pandya, et al.; "Where in the Brain Is Depression?"; Curr. Psychiatry Rep.; vol. 14, pp. 634-642 (2012).
Stonehouse, et al.; "Caffeine Regulates Neuronal Expression of the Dopamine 2 Receptor Gene"; Molecular Pharmacology; vol. 64, No. 6, pp. 1463-1473 (2003).

Aebischer, et al. "Long-Term Cross-Species Brain Transplantation of a Polymer-Encapsulated Dopamine-Secreting Cell Line", Experimental Neurology, 1991, vol. 111, pp. 269-275.
Ahmad, et al. "The *Drosophila rhodopsin* cytoplasmic tail domain is required for maintenance of rhabdomere structure." The FASEB Journal, 2007, vol. 21, p. 449-455.
Airan, et al., "Temporally Precise in vivo Control of Intracellular Signaling", 2009, Nature, vol. 458, No. 7241, pp. 1025-1029.
Akirav, et al. "The role of the medial prefrontal cortex-amygdala circuit in stress effects on the extinction of fear", Neural Plasticity, 2007: vol. 2007 Article ID:30873, pp. 1-11.
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the cre Gene Mediated by Cre Recombinase Using a Combination of Mutant lox Sites", Nucleic Acids Research, 2002, vol. 30, No. 19, pp. 1-8.
Aravanis, et al. "An optical neural interface: in vivo control of rodent motor cortex with integrated fiberoptic and optogenetic technology," J. Neural. Eng., 2007, vol. 4(3):S143-S156.
Argos, et al. "The integrase family of site-specific recombinases: regional similarities and global diversity", The EMBO Journal, 1986, vol. 5, No. 2, pp. 433-440.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Basil et al. "Is There Evidence for Effectiveness of Transcranial Magnetic Stimulation in the Treatment of Psychiatric Disorders?" Psychiatry, 2005, pp. 64-69.
Bebbington et al., "The use of vectors based on gene amplification for the expression of cloned genes in mammalian cells in DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berridge et al., "The Versatility and Universality of Calcium Signaling", Nature Reviews: Molecular Cell Biology, 2000, vol. 1: pp. 11-21.
Bocquet et al. "A prokaryotic proton-gated ion channel from the nicotinic acetylcholine receptor family." Nature Letters, 2007, vol. 445, p. 116-119.
Boyden, et al. "Millisecond-timescale, genetically targeted optical control of neural activity" Nature Neuroscience, 2005, vol. 8, No. 9: pp. 1263-1268.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-10472.
Blomer et al., "Highly Efficient and Sustained Gene Transfer in Adult Neurons with Lentivirus Vector", Journal of Virology,1997, vol. 71, No. 9: pp. 6641-6649.
Braun, "Two Light-activated Conductances in the Eye of the Green Alga Volvox carteri", 1999, Biophys J., vol. 76, No. 3, pp. 1668-1678.
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.

(56) References Cited

OTHER PUBLICATIONS

Brown, et al. "Long-term potentiation induced by θ frequency stimulation is regulated by a protein phosphate-operated gate." The Journal of Neuroscience, 2000, vol. 20, No. 21, pp. 7880-7887.
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods, 2008, vol. 169, Issue 1. Abstract only.
Cardin, et al. "Driving Fast spiking Cells Induces Gamma Rhythm and Controls Sensory Responses", 2009, Nature, vol. 459, vol. 7247, pp. 663-667.
Cenatiempo "Prokaryotic gene expression in vitro: transcription-translation coupled systems", Biochimie, 1986, vol. 68(4): pp. 505-515.
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Crouse, et al. "Expression and amplification of engineered mouse dihydrofolate reductase minigenes" Mol. Cell. Biol., 1983, vol. 3(2): pp. 257-266.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cucchiaro et al., "Electron-Microsoft Analysis of Synaptic Input from the Perigeniculate Nucleus to A-Lamine of the Lateral Geniculate Nucleus in Cats", The Journal of Comparitive Neurology, 1991, vol. 310, pp. 316-336.
Cui, et al., "Electrochemical deposition and characterization of conducting polymer polypyrrole/PSS on multichannel neural probes," Sensors and Actuators, 2001, vol. 93(1): pp. 8-18.
Date, et al. "Grafting of Encapsulated Dopamine-Secreting Cells in Parkinson's Disease: Long-Term Primate Study", Cell Transplant, 2000, vol. 9, pp. 705-709.
Dalva, et al. "Rearrangements of Synaptic Connections in Visual Cortex Revealed by Laser Photostimulation", Science, 1994,vol. 265, pp. 255-258.
Dederen, et al. "Retrograde neuronal tracing with cholera toxin B subunit: comparison of three different visualization methods", Histochemical Journal, 1994, vol. 26, pp. 856-862.
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Translocation of Calmodulin to the Nucleus Supports CREB Phosphorylation in Hippocampal Neurons", Nature, 1998, vol. 392, pp. 198-202.
Deisseroth et al., "Signaling from Synapse to Nucleus: the logic Behind the Mechanisms", Currrent Opinion in Neurobiology, 2003, vol. 13, pp. 354-365.
Deisseroth et al., "Excitation-neurogenesis Coupling in Adult Neural Stem/Progenitor Cells", 2004, Neuron, vol. 42, pp. 535-552.
Deisseroth "Next-generation optical technologies for illuminating genetically targeted brain circuits," The Journal of Neuroscience, 2006, vol. 26, No. 41, pp. 10380-10386.
Denk, W., et al. "Anatomical and functional imaging of neurons using 2-photon laser scanning microscopy", Journal of Neuroscience Methods, 1994, vol. 54, pp. 151-162.

Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 10I, No. 52, pp. 18206-18211.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Eisen, "Treatment of amyotrophic lateral sclerosis", Drugs Aging, 1999; vol. 14, No. 3, pp. 173-196.
Ernst, et al. "Photoactivation of Channelrhodopsin", 2008, vol. 283, No. 3, pp. 1637-1643.
Evanko "Optical excitation yin and yang" Nature Methods, 2007, 4:384.
Esposito et al. "The integrase family of tyrosine recombinases: evolution of a conserved active site domain", Nucleic Acids Research, 1997, vol. 25, No. 18, pp. 3605-3614.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Genbank Accession No. DQ094781 (Jan. 15, 2008).
Gelvich et al. "Contact flexible microstrip applicators (CFMA) in a range from microwaves up to short waves," IEEE Transactions on Biomedical Engineering, 2002, vol. 49, Issue 9: 1015-1023.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al. "Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gonzalez, et al., "Cell-Based Assays and Instrumentation for Screening Ion-Channel Targets", DDT, 1999, vol. 4, No. 9, pages 431439.
Gordon, et al. "Regulation of Thy-1 Gene Expression in Transgenic Mice", Cell, 1987, vol. 50, pp. 445-452.
Gorelova et al., "The course of neural projection from the prefrontal cortex to the nucleus accumbens in the rat ", Neuroscience, 1997, vol. 76, No. 3, pp. 689-706.
Gottesman et al."Bacterial regulation: global regulatory networks," Ann. Rev. Genet., 1984, vol. 18, pp. 415-441.
Gradinaru, et al. "ENpHR: a Natronomonas Halorhodopsin Enhanced for Optogenetic Applications", 2008, Brain Cell Biol., vol. 36 (1-4), pp. 129-139.

(56) References Cited

OTHER PUBLICATIONS

Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage ϕBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Hildebrandt et al, "Bacteriorhodopsin expressed in *Schizosaccharomyces pombe* pumps protons through the plasma membrane," PNAS, 1993, vol. 90, pp. 3578-3582.
Hirase, et al. "Multiphoton stimulation of neurons", J Neurobiol, 2002, vol. 51, No. 3: pp. 237-247.
Hodaie, et al. "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hosokawa, T. et al. "Imaging spatio-temporal patterns of long-term potentiation in mouse hippocampus." Philos. Trans. R. Soc. Lond. B., 2003, vol. 358, pp. 689-693.
Hynynen, et al. "Clinical applications of focused ultrasound—The brain." Int. J. Hyperthermia, 2007, vol. 23, No. 2: pp. 193-202.
International Search Report for International Application No. PCT/US2009/053474, dated Oct. 8, 2009.
Isenberg et al. "Cloning of a Putative Neuronal Nicotinic Aceylcholine Receptor Subunit," Journal of Neurochemistry, 1989, pp. 988-991.
Jekely, "Evolution of Phototaxis", 2009, Phil. Trans. R. Soc. B, vol. 364, pp. 2795-2808.
Johansen, et al., "Optical Activation of Lateral Amygdala Pyramidal Cells Instructs Associative Fear Learning", 2010, PNAS, vol. 107, No. 28, pp. 12692-12697.
Johnston et al. "Isolation of the yeast regulatory gene *GAL4* and analysis of its dosage effects on the galactose/melibiose regulon," PNAS, 1982, vol. 79, pp. 6971-6975.

Kandel, E.R., et al. "Electrophysiology of Hippocampal Neurons: I. Sequential Invasion and Synaptic Organization," J Neurophysiol, 1961, vol. 24, pp. 225-242.
Kandel, E.R., et al. "Electrophysiology of Hippocampal Neurons: II. After-Potentials and Repetitive Firing", J Neurophysiol., 1961, vol. 24, pp. 243-259.
Karreman et al. "On the use of double FLP recognition targets (FRTs) in the LTR of retroviruses for the construction of high producer cell lines" , Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khossravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kingston et al. "Transfection of DNA into Eukaryotic Cells," Supplement 63, Current Protocols in Molecular Biology, 1996, 9.1.1-9.1.11, 11 pages.
Kingston et al. "Transfection and Expression of Cloned DNA," Supplement 31, Current Protocols in Immunology, 1999, 10.13.1-10.13.9.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in Vivo", Nature, 2003, vol. 421: pp. 844-848.
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Knopfel, et al. "Optical Probin of Neuronal Circuit Dynamics: Gentically Encoded Versus Classical Fluorescent Sensors", 2006, Trends Neurosci, vol. 29, No. 3, pp. 160-166.
Kuhlman et al. (2008) "High-Resolution Labeling and Functional Manipulation of Specific Neuron Types in Mouse Brain by Cre-Activated Viral Gene Expression" PLoS One, 2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Landy, A. "Mechanistic and structural complexity in the site-specific recombination pathways of Int and FLP", Current Opinion in Genetics and Development, 1993, vol. 3, pp. 699-707.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gone Therapy Can Prevent Neuron Deatch Resulting from Necrotic and Apoptotic Insults", Journal of Neurochemistry, 2003, vol. 85: pp. 1079-1088.

(56) References Cited

OTHER PUBLICATIONS

Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992, vol. 9, pp. 861-871.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of FRT sites in the maize genome," Nucleic Acids Research, 1996, vol. 24, No. 19: pp. 3784-3789.
Ma et al. "Role of ER Export Signals in Controlling Surface Potassium Channel Numbers," Science, 2001, vol. 291, pp. 316-319.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging, 2001, vol. 24, No. 3, pp. 366-372.
Monje et al., "Irradiation Induces Neural Precursor-Cell Dysfunction", Natural Medicine, 2002, vol. 8, No. 9, pp. 955-962.
Mortensen et al. "Selection of Transfected Mammalian Cells," Supplement 86, Current Protocols in Molecular Biology, 1997, 9.5.1-09.5.19.
Nacher, et al. "NMDA receptor antagonist treatment increases the production of newneurons in the aged rat hippocampus", Neurobiology of Aging, 2003,vol. 24, No. 2: pp. 273-284.
Nagel et al. "Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using *Drosophila* Rh1-bovine rhodopsin chimeras," Vision Res., 2006, vol. 46, No. 27: pp. 4575-4581.
Nirenberg, et al. "The Light Response of Retinal Ganglion Cells is Truncated by a Displaced Amacrine Circuit", Neuron, 1997, vol. 18: pp. 637-650.
Nunes-Duby, et al. "Similarities and differences among 105 members of the Int family of site-specific recombinases", Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Palmer et al., "The Adult Rat Hippocampus Contains Primordial Neural Stem Cells", Molecular and Cellular Neuroscience, 1997, vol. 8, pp. 389-404.
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Pan et al. "Functional Expression of a Directly Light-Gated Membrane Channel in Mammalian Retinal Neurons: A Potential Strategy for Restoring Light Sensitivity to the Retina After Photoreceptor Degeneration,"Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1.I-9.1 1.I 8.
Peterlin, et al. "Optical probing of neuronal circuits with calcium indicators," PNAS, 2000, vol. 97, No. 7: pp. 3619-3624.
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Qiu et al. "Induction of photosensitivity by heterologous expression of melanopsin", Nature, 2005, vol. 433: pp. 745-749.
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Rathnasingham et al., "Characterization of implantable microfabricated fluid delivery devices," IEEE Transactions on Biomedical Engineering, 2004, vol. 51, No. 1: pp. 138-145.

(56) References Cited

OTHER PUBLICATIONS

Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.

Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.

Rosenkranz, et al. "The prefrontal cortex regulates lateral amygdala neuronal plasticity and responses to previously conditioned stimuli", J. Neurosci., 2003, vol. 23, No. 35: pp. 11054-11064.

Rousche, et al., "Flexible polyimide-based intracortical electrode arrays with bioactive capability," IEEE Transactions on Biomedical Engineering, 2001, vol. 48, No. 3, pp. 361-371.

Rubinson et at. "A lentivirus-based system to functionally silence genes in primary mammalian cells, stem cells and transgenic mice by RNA interference," Nature Genetics, 2003, vol. 33, p. 401-406.

Rudiger et at. "Specific arginine and threonine residues control anion binding and transport in the light-driven chloride pump halorhodopsin," The EMBO Journal, 1997, vol. 16, No. 13, pp. 3813-3821.

Salzman, et al. "Cortical microstimulation influences perceptual judgements of motion direction", Nature, 1990, vol. 346, pp. 174-177.

Sajdyk, et al., "Excitatory Amino Acid Receptors in the Basolateral Amygdala Regulate Anxiety Responses in the Social Interaction Test", Brain Research, 1997, vol. 764, pp. 262-264.

Sato et al. "Role of Anion-binding Sites in cytoplasmic and extracellular channels of *Natronomonas pharaonis* halorhodopsin," Biochemistry, 2005. vol. 44, pp. 4775-4784.

Sauer "Site-specific recombination: developments and applications," Current Opinion in Biotechnology, 1994, vol. 5, No. 5: pp. 521-527.

Schiff, et al. "Behavioral improvements with thalamic stimulation after severe traumatic brain injury," Nature, 2007, vol. 448, pp. 600-604.

Schlaepfer et al. "Deep Brain stimulation to Reward Circuitry Alleviates Anhedonia in Refractory Major Depression," Neuropsychopharmacology, 2008, vol. 33, pp. 368-377.

Sclimenti, et al. "Directed evolution of a recombinase for improved genomic integration at a native human sequence," Nucleic Acids Research, 2001, vol. 29, No. 24: pp. 5044-5051.

Shepherd, et al. "Circuit Analysis of Experience-Dependent Plasticity in the Developing Rat Barrel Cortex", Neuron, 2003, vol. 38: pp. 277-289.

Shibasaki et al. "Effects of body temperature on neural activity in the hippocampus: Regulation of resting membrane potentials by transient receptor potential vanilloid 4," The Journal of Neuroscience, 2007, vol. 27, No. 7: pp. 1566-1575.

Silver, et al. "Amino terminus of the yeast GAL4 gene product is sufficient for nuclear localization" PNAS, 1984, vol. 81, No. 19: pp. 5951-5955.

Singer et al. "Elevated Intrasynaptic Dopamine Release in Tourette's Syndrome Measured by PET," American Journal of Psychiatry, 2002, vol. 159: pp. 1329-1336.

Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.

Smith et al. "Diversity in the serine recombinases", Molecular Microbiology, 2002, vol. 44, No. 2: pp. 299-307.

Song et al. "Differential Effect of TEA on Long-Term Synaptic Modification in Hippocampal CA1 and Dentate Gyrus in Vitro." Neurobiology of Learning and Memory, 2001, vol. 76, No. 3, pp. 375-387.

Song, "Genes responsible for native depolarization-activated K+ currents in neurons," Neuroscience Research, 2002, vol. 42, pp. 7-14.

Stark, et al. "Catalysis by site-specific recombinases," Trends Genet., 1992, vol. 8, No. 12: pp. 432-439.

Stockklausner et al. "A sequence motif responsible for ER export and surface expression of Kir2.0 inward rectifier K+ channels," FEBS Letters, 2001, vol. 493, pp. 129-133.

Stoll, et al. "Phage TP901-I site-specific integrase functions in human cells," Journal of Bacteriology, 2002, vol. 184, No. 13: pp. 3657-3663.

Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.

Swiss-Prot_Q2QCJ4, Opsin 1, Oct. 31, 2006, URL: http://www.ncbi.nlm.nig.gov/protein/Q2QCJ4.

Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.

Tatarkiewicz, et al. "Reversal of Hyperglycemia in Mice After Subcutaneous Transplantation of Macroencapsulated Islets", Transplantation, 1999, vol. 67, No. 5: pp. 665-671.

Tottene et al., "Familial Hemiplegic Migraine Mutations Increase $Ca^{2+}$ Influx Through Single Human $Ca_v$ 2.1 Current Density in Neurons", PNAS USA, 2002, vol. 99, No. 20: pp. 13284-13289.

Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.

[No Authors Listed] "Two bright new faces in gene therapy," Nature Biotechnology, 1996, vol. 14: p. 556.

Tye et. al., "Amygdala circuitry mediating reversible and bidirectional control of anxiety", Nature, 2011, vol. 471(7338): pp. 358-362.

Tye et. al., Supplementary Materials: "An optically-resolved microcircuit for bidirectional anxiety control", Nature, 2011, vol. 471(7338): pp. 358-362.

"SubName: Full=Channelrhodopsin-1", retrieved from EBI accession No. UNIPROT: B4Y103. Database accession No. B4Y103. Sep. 23, 2008.

Ulmanen, et al. "Transcription and translation of foreign genes in *Bacillus subtilis* by the aid of a secretion vector," Journal of Bacteriology, 1985, vol. 162, No. 1: pp. 176-182.

Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.

Vanin, et al. "Development of high-titer retroviral producer cell lines by using Cre-mediated recombination," Journal of Virology, 1997, vol. 71, No. 10: pp. 7820-7826.

Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.

Wagner, "Noninvasive Human Brain Stimulation", Annual Rev. Biomed. Eng. 2007. 9:19.1-19.39.

Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.

Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.

Wang et al. "Direct-current Nanogenerator Driven by Ultrasonic Waves," Science, 2007, vol. 316, pp. 102-105.

Wang et. al., "High-speed mapping of synaptic connectivity using photostimulation in Channelrhodopsin-2 transgenic mice", PNAS, 2007, vol. 104, No. 19, pp. 8143-8148.

Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.

Wells et al. "Application of Infrared light for in Vivo neural stimulation," Journal of Biomedical Optics, 2005, vol. 10(6), pp. 064003-1-064003-12.

(56) References Cited

OTHER PUBLICATIONS

Witten et. al., Supporting Online Material for: "Cholinergic Interneurons Control Local Circuit Activity and Cocaine Conditioning", Science, 2010, vol. 330: 17 pages.
Witten et. al., "Cholinergic Interneurons Control Local Circuit Activity and Cocaine Conditioning", Science, 2010, vol. 330, No. 6011: pp. 1677-1681.
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human β, β-Carotene-15, 15'-Dioxygenase that is Highly Expressed in the Retinal Pigment Epithelium", Genomics, 2001, vol. 72: pp. 193-202.
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang, et al. "Channelrhodopsin-2 and optical control of excitable cells," Nature Methods, 2006, vol. 3, No. 10, pp. 785-792.
Zhang, et al. "Red-Shifted Optogenetic Excitation: a Tool for Fast Neural Control Derived from *Volvox carteri* ", Nature Neurosciences, 2008, vol. 11, No. 6, pp. 631-633.
Zhang "Multimodal fast optical interrogation of neural circuitry," Nature, 2007, vol. 446, pp. 633-641.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient in Vivo Gene Delivery", Journal of Virology, 1998, vol. 72, No. 12, pp. 9873-9880.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Definition of Psychosis (2015).
Ebert et al., "A Moloney MLV-rat somatotropin fusion gene produces biologically active somatotropin in a transgenic pig", Mol. Endocrinology, 1988, vol. 2, pp. 277-283.
Hammer et al., "Spontaneous inflammatory disease in transgenic rats expressing HLA-B27 and Human $β_2$ m: an animal model of HLA-B27-associated human disorders", Cell, 1990, vol. 63, pp. 1099-1112.
Karra, et al. "Transfection Techniques for Neuronal Cells", The Journal of Neuroscience, 2010, vol. 30, No. 18, pp. 6171-6177.
Kelder et al., "Glycoconjugates in human and transgenic animal milk", Advances in Exp. Med. and Biol., 2001, vol. 501, pp. 269-278.
Mullins et al., "Fulminant hypertension in transgenic rats harbouring the mouse Ren-2 gene", Nature, 1990, vol. 344, pp. 541-544.
Mullins et al., "Expression of the DBA/2J Ren-2 gene in the adrenal gland of transgenic mice", EMBO, 1989, vol. 8, pp. 4065-4072.

Taurog et al., "HLA-B27 in inbred and non-inbred transgenic mice", J. Immunol., 1988, vol. 141, pp. 4020-4023.
Wall, "Transgenic livestock: Progress and prospects for the future", Theriogenology, 1996, vol. 45, pp. 57-68.
Wang, et al., "High-speed mapping of synaptic connectivity using photostimulation in Channelrhodopsin-2 transgenic mice", Proceedings of the National Academy of Sciences, 2007, vol. 104, No. 19, pp. 8143-8148.
Written opinion of PCT Application No. PCT/US2011/059383 (May 9, 2012).
Clark, et al.; "A future for transgenic livestock"; Nature Reviews Genetics; vol. 4, No. 10, pp. 825-833 (Oct. 2003).
Do Carmo, et al.; "Modeling Alzheimer's disease in transgenic rats"; Molecular Neurodegeneration; vol. 8, No. 37, 11 pages (2013).
Heymann, et al.; "Expression of Bacteriorhodopsin in Sf9 and COS-1 Cells"; Journal of Bioenergetics and Biomembranes; vol. 29, No. 1, pp. 55-59 (1997).
Ramalho, et al.; "Mouse genetic corneal disease resulting from transgenic insertional mutagenesis"; Br. J. Ophthalmol.; vol. 88, No. 3, pp. 428-432 (Mar. 2004).
Ristevski; "Making Better Transgenic Models: Conditional, Temporal, and Spatial Approaches"; Molecular Biotechnology; vol. 29, No. 2, pp. 153-163 (Feb. 2005).
Sigmund; "Viewpoint: Are Studies in Genetically Altered Mice Out of Control?"; Arterioscler Thromb Vasc. Biol.; vol. 20, No, 6, pp. 1425-1429 (Jun. 2000).
Sineshchekov et al.; "Intramolecular Proton Transfer in Channelrhodopsins"; Biophysical Journal; vol. 104, No. 4, pp. 807-807 (Feb. 2013).
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Takahashi, et al., "Induction of Pluripotent Stem Cells from Mouse Embryonic and Adult Fibroblast Cultures by Defined Factors", 2006, Cell, vol. 126, pp. 663-676.
Hikida et al., "Increased sensitivity to cocaine by cholinergic cell ablation in nucleus accumbens", PNAS, Nov. 2001, 98(23): 13351-13354.
Hikida et al., "Acetylcholine enhancement in the nucleus accumbens prevents addictive behaviors of cocaine and morphine", PNAS, May 2003, 100(10):6169-6173.
Kitabatake et al., "Impairment of reward-related learning by cholinergic cell ablation in the striatum", PNAS, Jun. 2003, 100(13):7965-7970.
Tamai, "Progress in Pathogenesis and Therapeutic Research in Retinitis Pigmentosa and Age Related Macular Degeneration", Nippon Ganka Gakkai Zasshi, vol. 108, No. 12, Dec. 2004 (Dec. 2004), pp. 750-769.
Fiala et al., "Optogenetic approaches in neuroscience", Current Biology, Oct. 2010, 20(20):R897-R903.
Gradinaru et al., "Optical deconstruction of parkinsonian neural circuitry", Science, Apr. 2009, 324(5925):354-359.
Liu et al., "Optogenetics 3.0", Cell, Apr. 2010, 141(1):22-24.
Malin et al., "Involvement of the rostral anterior cingulate cortex in consolidation of inhibitory avoidance memory: Interaction with the basolateral amygdala", Neurobiol Learning Mem, 2007, 87(2):295-302.
Mayford et al., "Control of memory formation through regulated expression of CAMKII Transgene", Science, Dec. 1996, 274:1678-1683.
Schroll et al., "Light-induced activation of distinct modulatory neurons triggers appetitive or aversive learning in *Drosophila* larvae", Current Biology, Sep. 2006, 16(17):1741-1747.
Fox et al., "A gene neuron expression fingerprint of C. elegans embryonic motor neurons", BMC Genomics, 2005, 6(42):1-23.
Nonet, "Visualization of synaptic specializations in live C. elegans with synaptic vesicle protein-GFP fusions", J. Neurosci. Methods, 1999, 89:33-40.
Synapse, Chapter 13, http://michaeldmann.net/mann13.html, downloaded Apr. 2014.

(56) References Cited

OTHER PUBLICATIONS

Cazillis et al., "VIP and PACAP induce selective neuronal differentiation of mouse embryonic stem cells", Eur J Neurosci, 2004, 19(4):798-808.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Tye, et al. "Optogenetic investigation of neural circuits underlying brain disease in animal models," Nature Reviews Neuroscience (Mar. 2012), 13(4):251-266.
Berke, et al. "Addiction, Dopamine, and the Molecular Mechanisms of Memory", Molecular Plasticity, 2000, vol. 25: pp. 515-532.
Goshen et al. "Dynamics of Retrieval Strategies for Remote Memories", Cell, 2011, vol. 147: pp. 678-589.
Jimenez S.A & Maren S. et all "Nuclear disconnection within the amygdala reveals a direct pathway to fear", Learning Memory, 2009, vol. 16: pp. 766-768.
Ehrlich I. et al. "Amygdala inhibitory circuits and the control of fear memory", Neuron, 2009. Friedrich Meischer Institute, vol. 62: pp. 757-771.
Berndt et al. "Bi-stable neural state switches", Nature Neuroscience, 2009, vol. 12, No. 2: pp. 229-234.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Davis; "The many faces of epidermal growth factor repeats," The New Biologist; vol. 2, No. 5, pp. 410-419 (1990).
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
EBI accession No. UNIPROT: A7U0Y6; "SubName: Full=Bacteriorhodopsin"; (Aug. 10, 2010).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
Kaiser; "Clinical research. Death prompts a review of gene therapy vector"; Science; 317(5838):580 (Aug. 3, 2007).
Kay; "State-of-the-art gene-based therapies: the road ahead"; Nature Reviews Genetics; vol. 12, pp. 316-328 (May 2011).
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Soofiyan I, et al.; "Gene Therapy, Early Promises, Subsequent Problems, and Recent Breakthroughs"; Advanced Pharmaceutical Bulletin; vol. 3, No. 2, pp. 249-255 (2013).
U.S. Appl. No. 13/555,981, filed Jul. 23, 2012, Deisseroth, et al.
U.S. Appl. No. 13/622,809, filed Sep. 19, 2012, Deisseroth, et al.
U.S. Appl. No. 13/623,612, filed Sep. 20, 2012, Deisseroth, et al.
U.S. Appl. No. 13/718,243, filed Dec. 18, 2012, Deisseroth, et al.
U.S. Appl. No. 13/763,119, filed Feb. 8, 2013, Deisseroth, et al.
U.S. Appl. No. 13/772,732, filed Feb. 21, 2013, Deisseroth, et al.
U.S. Appl. No. 13/847,653, filed Mar. 20, 2013, Deisseroth, et al.
U.S. Appl. No. 13/847,785, filed Mar. 20, 2013, Deisseroth, et al.
U.S. Appl. No. 13/849,913, filed Mar. 25, 2013, Deisseroth, et al.
U.S. Appl. No. 13/850,426, filed Mar. 26, 2013, Deisseroth, et al.
U.S. Appl. No. 13/850,428, filed Mar. 26, 2013, Deisseroth, et al.
U.S. Appl. No. 13/850,436, filed Mar. 26, 2013, Deisseroth, et al.
U.S. Appl. No. 13/850,709, filed Mar. 26, 2013, Deisseroth, et al.
U.S. Appl. No. 13/854,750, filed Apr. 1, 2013, Deisseroth, et al.
U.S. Appl. No. 13/854,754, filed Apr. 1, 2013, Deisseroth, et al.
U.S. Appl. No. 13/855,413, filed Apr. 2, 2013, Deisseroth, et al.
U.S. Appl. No. 13/875,966, filed May 2, 2013, Deisseroth, et al.
U.S. Appl. No. 13/882,566, filed Nov. 4, 2011, Deisseroth, et al.
U.S. Appl. No. 13/882,666, filed Nov. 4, 2011, Deisseroth, et al.
U.S. Appl. No. 13/882,670, filed Nov. 4, 2011, Deisseroth, et al.
U.S. Appl. No. 13/882,703, filed Nov. 4, 2011, Deisseroth, et al.
U.S. Appl. No. 13/882,705, filed Nov. 4, 2011, Deisseroth, et al.
U.S. Appl. No. 13/882,719, filed Nov. 4, 2011, Deisseroth, et al.
Tam, B. et al., "Identification of an Outer Segment Targeting Signal in the COOH Terminus of Rhodopsin Using Transgenic Xenopus laevis", The Journal of Cell Biology, 2000, vol. 151, No. 7, pp. 1369-1380.
Brewin; "The Nature and Significance of Memory Disturbance in Posttraumatic Stress Disorder"; Ann. Rev. Clin. Psychol.; vol. 7, pp. 203-227 (2011).
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sept.-Oct. 2003).
Samuelson; "Post-traumatic stress disorder and declarative memory functioning: a review"; Dialogues in Clinical Neuroscience; vol. 13, No. 3, pp. 346-351 (2011).
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Han, et al., "Multiple-Color Optical Activation, Silencing, and Desynchronization of Neural Activity with Single-Spike Temporal Resolution", PLoS One, 2007, vol. 2, No. 3, pp. 1-12.
Kinoshita, et al., "Optogenetically Induced Supression of Neural Activity in the Macaque Motor Cortex", Poster Sessions Somatomotor System, Others,2010, pp. 141-154.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Tsai, et al., "Phasic Firing in Dopaminergic Neurons in Sufficient for Behavioral Conditioning", Science, 2009, vol. 324, pp. 1080-1084.
Zhao, et al., "Improved Expression of Halorhodopsin for Light-Induced Silencing of Neuronal Activity", Brain Cell Biology, 2008, vol. 36 (1-4), pp. 141-154.
Lanyi et al. "The primary structure of a Halorhodopsin from *Natronobacterium pharaonis*" Journal of Biological Chemistry 1990, vol. 265, No. 3, p. 1253-1260.
Hofherr et al. "Selective Golgi export of Kir2.1 controls the stoichiometry of functional Kir2.x channel heteromers"Journal of Cell Science, 2005, vol. 118, p. 1935-1943.
Loetterle, et al., "Cerebellar Stimulation: Pacing the Brain", American Journal of Nursing, 1975, vol. 75, No. 6, pp. 958-960.
Balint, et al., "The Nitrate Transporting Photochemical Reaction Cycle of the Pharaonis Halorhodopsin", Biophysical Journal, 2004, vol. 86, pp. 1655-1663.
Gradinaru, et al., Molecular and Cellular Approaches for Diversifying and Extending Optogenetics, Cell, 2010, vol. 141, No. 1, pp. 154-165.
RecName: Full=Halorhodopsin; Short=HR; Alt Name: Full=NpHR; XP002704922, retrieved from EBI accession No. UNIPROT: P15647. Database accession No. P15647. Apr. 1, 1990.
"N. pharaonis halorhodopsin (hop) gene, complete cds.", XP002704883, retrieved from EBI accession No. EMBL: J05199. Database accession No. J05199. Nov. 22, 1990.
"Subname: Fluu=Bacteriorhodopsin"; XP002704863, retrieved from EBI accession No. UNIPROT: BOR5N9. Database accession No. BOR5N9. Apr. 8, 2008.
Zhang, et al., "The Microbial Opsin Family of Optogenetic Tools", Cell, 2011, vol. 147, No. 7, pp. 1146-1457.
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Asano, et al.; "Optically Controlled Contraction of Photosensitive Skeletal Muscle Cells"; Biotechnology & Bioengineering; vol. 109, No. 1, pp. 199-204 (Jan. 2012).
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascu-

(56) References Cited

OTHER PUBLICATIONS lar smooth muscle cells in vitro and in vivo"; European Heart Journal; vol. 32, No. Suppl . 1, p. 997 (Aug. 2011).
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
Genbank Accession No. BAA09452.1; Mukohata et al.; pp. 1 (Feb. 10, 1999).
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Mueller, et al.; "Clinical Gene Therapy Using Recombinant Adeno-Associated Virus Vectors"; Gene Therapy; vol. 15, pp. 858-863 (2008).
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Gradinaru et al., "Targeting and readout strategies for fast optical neural control in Vitro and in Vivo", J Neuroscience, 2007, 27(52):14231-14238.
Han, et al., "Millisecond-Timescale Optical Control of Neural Dynamics in the Nonhuman Primate Brain"; Neuron; vol. 62, pp. 191-198 (Apr. 30, 2009).
Han, et a.; "Virogenetic and optogenetic mechanisms to define potential therapeutic targets in psychiatric disorders"; Neuropharmacology; vol. 62, pp. 89-100 (2012).
Zhang, et al.; "Optogenetic interrogation of neural circuits: Technology for probing mammalian brain structures"; Nature Protocols; vol. 5, No. 3, pp. 439-456 (Mar. 1, 2010).
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Fenno et al., "The development and application of optogenetics", Annual Review of Neuroscience, 2011, vol. 34, No. 1, pp. 389-412.
Gunaydin et al., "Ultrafast optogenetic control", Nature Neuroscience, 2010, vol. 13, No. 3, pp. 387-392.
Hira et al., "Transcranial optogenetic stimulation for functional mapping of the motor cortex", J Neurosci Methods, 2009, vol. 179, pp. 258-263.
Lalumiere, R., "A new technique for controlling the brain: optogenetics and its potential for use in research and the clinic", Brain Stimulation, 2011, vol. 4, pp. 1-6.
Lin, "A user's guide to channelrhodopsin variants: features, limitations and future developments", Exp Physiol, 2010, vol. 96, No. 1, pp. 19-25.
Mancuso et al., "Optogenetic probing of functional brain circuitry", Experimental Physiology, 2010, vol. 96.1, pp. 26-33.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Pinkham et al., "Neural bases for impaired social cognition in schizophrenia and autism spectrum disorders", Schizophrenia Research, 2008, vol. 99, pp. 164-175.
Sohal et al., "Parvalbumin neurons and gamma rhythms enhance cortical circuit performance", Nature, 2009, vol. 459, No. 7247, pp. 698-702.
Yizhar et al., "Optogenetics in neural systems", Neuron Primer, 2011, vol. 71, No. 1, pp. 9-34.
Li et al., "Surface Expression of Kv1 Channels is Governed by a C-Terminal Motif", J. Biol. Chem. (2000), 275(16):11597-11602.

Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Varo et al.," Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Deisseroth, et al., "Controlling the Brain with Light", Scientific American, 2010, vol. 303, pp. 48-55.
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Sineshchekov, et al., "Two Rhodopsins Mediate Phototaxis to Low and High Intensity Light in Chlamydomas Reinhardtil", PNAS, 2002, vol. 99, No. 13, pp. 8689-8694.
Tønnese, et al., "Optogenetic Control of Epileptiform Activity", PNAS, 2009, vol. 106, No. 29, pp. 12162-12167
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Berndt et al., "Structure-Guided Transformation of Channelrhodopsin into a Light-Activated Chloride Channel", Science (Apr. 2014), 344(6182):420-424.
Chow et al., "Optogenetics and Translational Medicine", Science Translational Medicine (Mar. 2013), 5(177):177ps5.
Eijkelkamp, et al. "Neurological perspectives on voltage-gated sodium channels", Brain (Sep. 2012), 135(Pt 9):2585-2612.
Garrido et al., "A targeting motif involved in sodium channel clustering at the axonal initial segment", Science (Jun. 2003), 300(5628):2091-4.
Han; et al., "Two-color, bi-directional optical voltage control of genetically-targeted neurons", CoSyne (2007), Abstract Presentation, Poster III-67, p. 269, Presented Feb. 24, 2007.
Hustler; et al., "Acetylcholinesterase staining in human auditory and language cortices: regional variation of structural features", Cereb Cortex (Mar.-Apr. 1996), 6(2):260-70.
Iyer et al., "Virally mediated optogenetic excitation and inhibition of pain in freely moving nontransgenic mice", Nat Biotechnol., (Mar. 2014), 32(3):274-8.
Ji et al., "Light-evoked Somatosensory Perception of Transgenic Rats that Express Channelrhodopsin-2 in Dorsal Root Ganglion Cells", PLoS One (2012), 7(3):e32699.
Jennings et al., "Distinct extended amygdala circuits for divergent motivational states," Nature (Apr. 2013), 496(7444):224-8.
Kim et al., "PDZ domain proteins of synapses", Nature Reviews Neuroscience, (Oct. 2004), 5(10):771-81.
Kim et al., "Diverging neural pathways assemble a behavioural state from separable features in anxiety"Nature (Apr. 2013), 496(7444):219-23.
Kokel et al., "Photochemical activation of TRPA1 channels in neurons and animals", Nat Chem Biol (Apr. 2013), 9(4):257-63.
Lammel et al., "Input-specific control of reward and aversion in the ventral tegmental area", Nature (Nov. 2012), 491(7423): 212-7.
Liske et al., "Optical inhibition of motor nerve and muscle activity in vivo", Muscle Nerve (Jun. 2013), 47(6):916-21.
Llewellyn et al., "Orderly recruitment of motor units under optical control in vivo", Nature Medicine, (Oct. 2010), 16(10):1161-5.
Mattis et al., "Principles for applying optogenetic tools derived from direct comparative analysis of microbial opsins", Nat Methods (Dec. 2011), 9(2):159-72.
Mourot et al., "Rapid Optical Control of Nociception with an Ion Channel Photoswitch", Nat Methods (Feb. 2012), 9(4):396-402.
Nieh et al., "Optogenetic dissection of neural circuits underlying emotional valence and motivated behaviors", Brain Research, (May 2012), 1511:73-92.
Slamovits et al., "A bacterial proteorhodopsin proton pump in marie eukaryotes", Nature Communications (Feb. 2011), 2:183.
Towne et al., "Efficient transduction of non-human primate motor neurons after intramuscular delivery of recombinant AAV serotype 6", Gene Ther. (Jan. 2010), 17(1):141-6.

(56) References Cited

OTHER PUBLICATIONS

Towne et al., "Optogenetic control of targeted peripheral axons in freely moving animals", PLoS One (Aug. 2013), 8(8):e72691.
Towne et al., "Recombinant adeno-associated virus serotype 6 (rAAV2/6)-mediated gene transfer to nociceptive neurons through different routes of delivery", Mol Pain (Sep. 2009), 5:52.
Wang et al., "Mrgprd-Expressing Polymodal Nociceptive Neurons Innervate Most Known Classes of Substantia Gelatinosa Neurons", J Neurosci (Oct. 2009), 29(42):13202-13209.
Williams et al., "From optogenetic technologies to neuromodulation therapies", Sci Transl Med. (Mar. 2013), 5(177):177ps6.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Day, et al.; "The Nucleus Accumbens and Pavlovian Reward Learning"; Neuroscientist; vol. 13, No. 2, pp. 148-159 (Apr. 2007).
Knopfel, et al.; "A comprehensive concept of optogenetics"; Progress in Brain Research; vol. 196, pp. 1-28 (2012).
Packer, et al.; "Targeting Neurons and Photons for Optogenetics"; Nature Neuroscience; vol. 16, No. 7, pp. 805-815 (Jul. 2013).
Babin et al., "Zebrafish Models of Human Motor Neuron Diseases: Advantages and Limitations", Progress in Neurobiology (2014), 118:36-58.
Santana et al., "Can Zebrafish Be Used as Animal Model to Study Alzheimer's Disease?" Am. J. Neurodegener. Dis. (2012), 1(1):32-48.
Sheikh et al., "Neurodegenerative Diseases: Multifactorial Conformational Diseases and Their Therapeutic Interventions", Journal of Neurodegenerative Diseases (2013), Article ID 563481:1-8.
Suzuki et al., "Stable Transgene Expression from HSV Amplicon Vectors in the Brain: Potential Involvement of Immunoregulatory Signals", Molecular Therapy (2008), 16(10):1727-1736.
Thomas et al., "Progress and Problems with the Use of Viral Vectors for Gene", Nat. Rev. Genet. (2003), 4(5):346-358.
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages (Jun. 2013).
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Jones, et al.; "Animal Models of Schizophrenia"; British Journal of Pharmacology; vol. 164, pp. 1162-1194 (2011).
Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Airan, et al.; "Integration of light-controlled neuronal firing and fast circuit imaging"; Current Opinion in Neurobiology; vol. 17, pp. 587-592 (2007).
Cannon, et al.; "Endophenotypes in the Genetic Analyses of Mental Disorders"; Annu. Rev. Clin. Psychol.; vol. 2, pp. 267-290 (2006).
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Deonarain; "Ligand-targeted receptor-mediated vectors for gene delivery"; Exp. Opin. Ther. Patents; vol. 8, No. 1, pp. 53-69 (1998).
Edelstein, et al.; "Gene therapy clinical trials worldwide 1989-2004—an overview"; The Journal of Gene Medicine; vol. 6, pp. 597-602 (2004).
Grady, et al.; "Age-Related Reductions in Human Recognition Memory Due to Impaired Encoding"; Science; vol. 269, No. 5221, pp. 218-221 (Jul. 14, 1995).
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Johnson-Saliba, et al.; "Gene Therapy: Optimising DNA Delivery to the Nucleus"; Current Drug Targets; vol. 2, pp. 371-399 (2001).
Palu, et al.; "In pursuit of new developments for gene therapy of human diseases"; Journal of Biotechnology; vol. 68, pp. 1-13 (1999).
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Pfeifer, et al.; "Gene Therapy: Promises and Problems"; Annu. Rev. Genomics Hum. Genet.; vol. 2, pp. 177-211 (2001).
Powell, et al.; "Schizophrenia-Relevant Behavioral Testing in Rodent Models: A Uniquely Human Disorder?"; Biol. Psychiatry; vol. 59, pp. 1198-1207 (2006).
Shoji, et al.; "Current Status of Delivery Systems to Improve Target Efficacy of Oligonucleotides"; Current Pharmaceutical Design; vol. 10, pp. 785-796 (2004).
Verma, et al.; "Gene therapy—promises, problems and prospects"; Nature; vol. 389, pp. 239-242 (Sep. 1997).
Wang, et al.; "Simultaneous phase and size control of upconversion nanocrystals through lanthanide doping"; Nature; vol. 463, No. 7284, pp. 1061-1065 (Feb. 25, 2010).
Ferenczi, et al.; "Optogenetic approaches addressing extracellular modulation of neural excitability"; Scientific Reports; vol. 6, 20 pages (Apr. 5, 2016).
Li, et al.; "A Method for Activiation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Definition of Implant; Merriam-Webster Dictionary; retrieved Nov. 7, 2016 (http://www.merriam-webster.com/dictionary/implant).
Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Davidson, et al.; "Viral Vectors for Gene Delivery to the Nervous System"; Nature Reviews Neuroscience; vol. 4, pp. 353-364 (May 2003).
Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Definition of integral. Merriam-Webster Dictionary, retrieved on Mar. 20 2017; Retrieved from the internet: <http://www.merriam-webster.com/dictionary/integral>.

\* cited by examiner

E

F

G

H

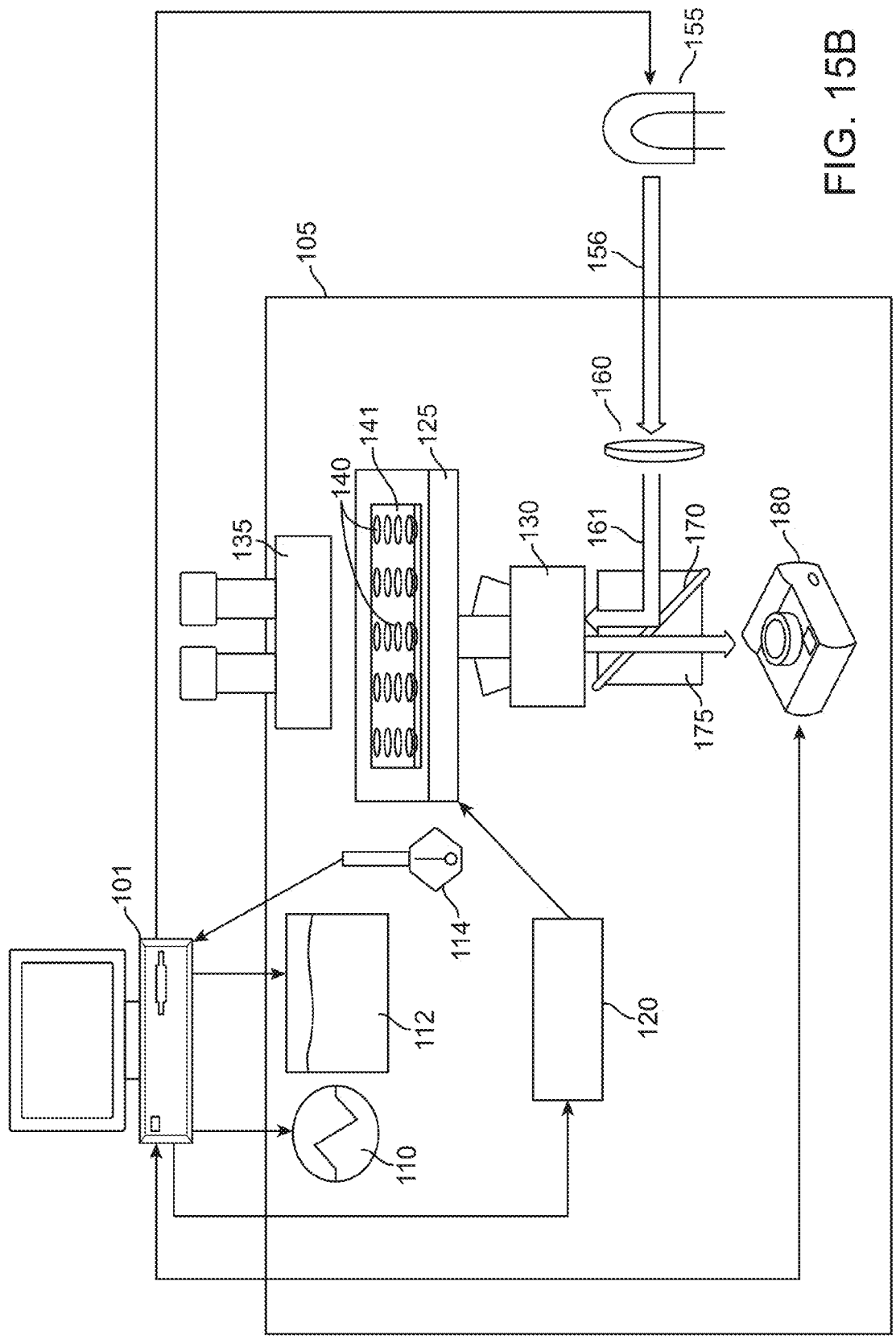

SYSTEM, METHOD AND APPLICATIONS INVOLVING IDENTIFICATION OF BIOLOGICAL CIRCUITS SUCH AS NEUROLOGICAL CHARACTERISTICS

CROSS-REFERENCE

This application is a continuation of U.S. patent application Ser. No. 12/031,651, filed Feb. 14, 2008, now U.S. Pat. No. 8,401,609, and claims the benefit of U.S. Provisional Patent Application No. 60/901,178, filed Feb. 14, 2007, which applications are incorporated herein by reference in their entirety.

STATEMENT REGARDING FEDERALLY SPONSORED RESEARCH

This invention was made with Government support under Grant No. OD000616 awarded by the National Institutes of Health. The Government has certain rights in the invention.

FIELD OF THE INVENTION

The present invention relates generally to imaging systems and methods, and more particularly to imaging of biological networks.

BACKGROUND

Understanding the complexities of biological tissue and its electrical behavior continues to be an area of ongoing research and study. For example, a major challenge facing psychiatry is the lack of understanding of the neuronal network changes that underlie clinical depression and recovery. The hippocampus is hypothesized to play a central role in both depression pathophysiology and treatment response, but the underlying local network dynamics are not understood, with studies yielding apparently contradictory findings.

Development of new treatments for psychiatric disorders is hindered by an almost complete lack of information on how maladaptive neural physiology may give rise to affective phenotypes. For this reason, identification of a neurophysiological final common pathway linked to the etiology of a psychiatric disease could revolutionize understanding and guide clinical development of novel treatments. In depression, a leading cause of disability that affects an estimated 121 million people worldwide, the current widely-used medications are often effective in reducing symptoms and can promote remission, but treatment-resistance to first-line antidepressants like the selective serotonin reuptake inhibitors (SSRIs, such as fluoxetine and paroxetine) occurs in up to 50% of patients. Well-known medication side effects further complicate compliance and recovery, pointing to the need for new classes of treatment. Development of new classes of treatment is severely constrained by the incomplete understanding of the multifactorial biological etiology of depression, which involves genetic predisposition, epigenetic and developmental alterations, and adverse life events including chronic or acute stress. If many of these different etiological factors are expressed behaviorally through final common neurophysiological features, identification of these putative endophenotypes could not only provide a basis for understanding of the disease but also enable rapid development of novel selective classes of antidepressant treatments.

Candidate neural structures pertinent to depression physiology have been identified in part by using structural and functional imaging. Human fMRI studies have demonstrated altered blood flow associated with depression in several brain regions, including specific components of the emotion-regulating limbic circuitry. In particular, the hippocampus has received considerable attention as an integral component of the limbic system that communicates directly with and drives other brain regions implicated in depression, such as the prefrontal cortex, hypothalamic-pituitary-adrenal (HPA) axis, and reward centers. A substantial body of work favors the concept that the hippocampus is hyperactive in depression.

PET imaging has been used in depressed patients to implicate overactive excitatory pathways radiating from the hippocampus to downstream cortical regions (e.g., to Cg25) which is thought to be overactive in depression, and to orbitofrontal cortex), and furthermore found that fluoxetine-induced reduction in hippocampal activity was tightly linked to successful clinical response. Meta-analysis of functional brain imaging in medication treatment of depression indicated that changes in downstream cortical regions are delayed until specific adaptive changes occur in the source of primary afferent inputs, e.g., the hippocampus. This work showed that the hippocampus is a "primary site of action" for major antidepressants and a key initiator of successful response to antidepressant treatment. Complicating this picture, however, is evidence suggesting reduced hippocampal activity in depression, including reduced hippocampal size in clinical depression, the fact that excitatory hippocampal neurons display atrophy and death due to chronic stress and stress hormone exposure, and the observation that antidepressant-induced production of presumed excitatory neurons in the dentate gyrus of the hippocampal formation is linked to behavioral efficacy.

SUMMARY

Aspects of the present invention involve the implementation of new optical technologies that allow sufficient spatial (pm) and temporal resolution (ms) of electrical activity in distinct neural circuits.

Consistent with one embodiment of the present invention, a method is implemented for assessing neural activity in a neural region having multiple subfields. An electrical response is evoked in at least one subfield due to neural activity in the neural region. Image data of the electrical response is captured at a level sufficiently detailed in space and time to differentiate between polarization-based events of two respective portions of the subfield. Neural activity is assessed by correlating space and time information, from the captured data, for the two respective portions of the subfield.

Consistent with one embodiment of the present invention, a method is implemented for assessing neural activity in a neuronal network that includes first and second portions electrically related to one another. The neuronal network is stained with a voltage sensitive dye. The first portion of the neuronal network is stimulated. Responsive to the stimulation, image data is captured that results from the voltage sensitive dye and neural activity in the first portion. The image data is processed to assess neural activity indicative of a disorder.

Consistent with one embodiment of the present invention, a system is implemented for determining neural activity in a neural region having multiple subfields. A preparation arrangement prepares the neural region for imaging. A stimulation arrangement stimulates at least one subfield in the neural region. An imaging device for captures image data resulting from stimulation of the neural region, wherein the image data is captured at a level sufficiently detailed in space and time to differentiate between polarization-based events of two respective portions of the subfield. A processor assesses neural activity by correlating space and time information, from the captured data, for the two respective portions of the sub-field.

Consistent with one embodiment of the present invention, an arrangement is implemented for use in a system for determining neural activity in a neural region having multiple subfields, the system including a preparation arrangement for preparing the neural region for imaging, a stimulation arrangement for stimulating at least one subfield in the neural region, and an imaging device capable of capturing image data resulting from stimulation of the neural region. The arrangement includes a processor programmed and adapted to process image data captured at a level sufficiently detailed in space and time to differentiate between polarization-based events of two respective portions of the subfield, to assess neural activity by correlating space and time information, from the captured data, for the two respective portions of the sub-field.

Consistent with one embodiment of the present invention, storage medium for use in a system for determining neural activity in a neural region having multiple subfields, the system including a preparation arrangement for preparing the neural region for imaging, a stimulation arrangement for stimulating at least one subfield in the neural region, and an imaging device capable of capturing image data resulting from stimulation of the neural region, a storage medium storing computer-executable data which, when executed by a computer arrangement, cause the computer arrangement to perform steps. A first step involves processing image data captured at a level sufficiently detailed in space and time to differentiate between polarization-based events of two respective portions of the subfield. A second step involves assessing neural activity by correlating space and time information, from the captured data, for the two respective portions of the sub-field.

The above summary of the present invention is not intended to describe each illustrated embodiment or every implementation of the present invention. The figures and detailed description that follow more particularly exemplify these embodiments.

BRIEF DESCRIPTION OF DRAWINGS

The invention may be understood in consideration of the detailed description of various embodiments of the invention that follows in connection with the accompanying drawings in which:

FIG. 15B shows a specific system diagram of a large-format, quasi-automated system for drug screening, according to an example embodiment of the present invention.

Figure 1:
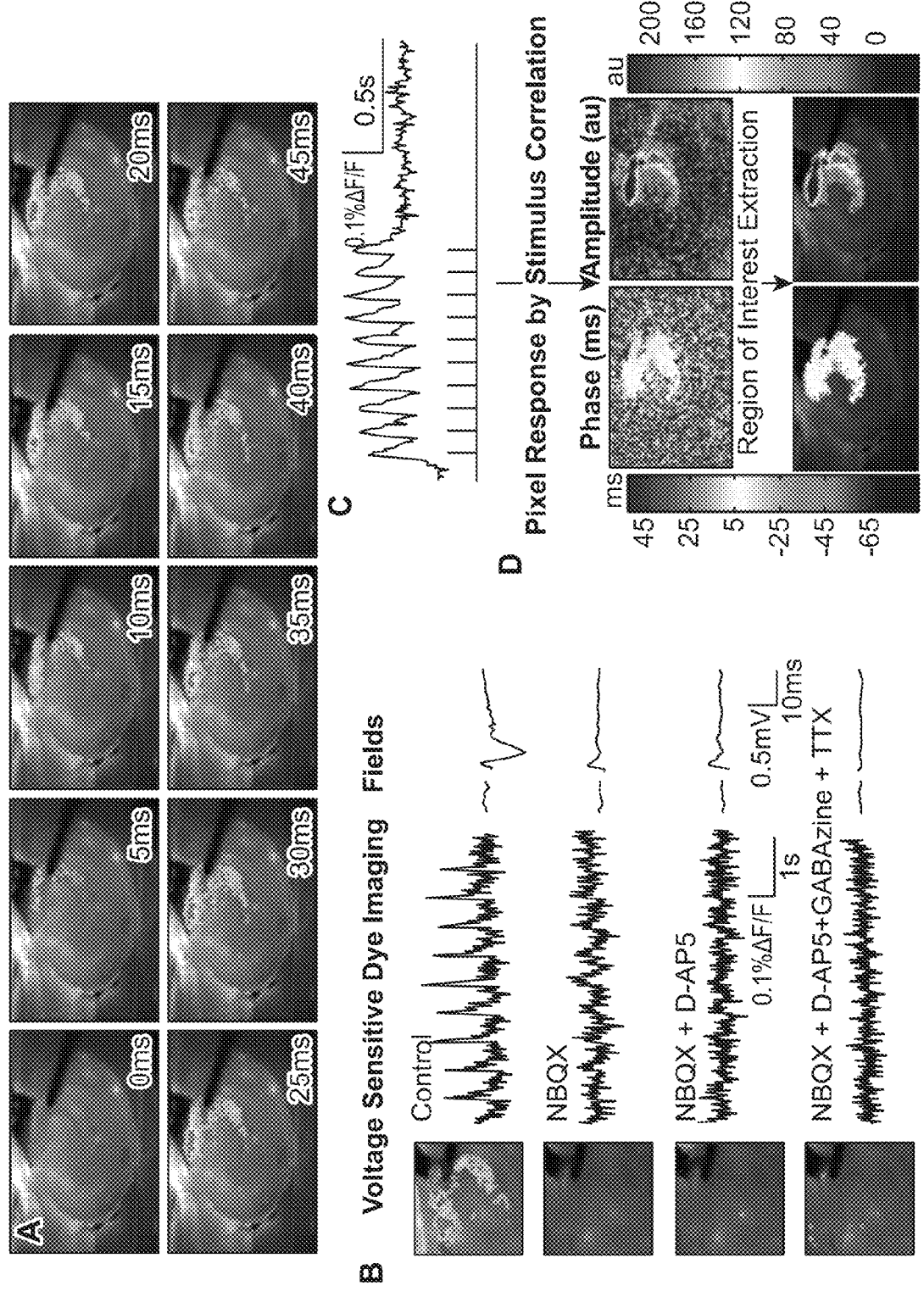
FIG. 1A shows representative filmstrip acquired using voltage-sensitive-dye imaging (VSDI), consistent with an example embodiment of the present invention.
FIG. 1B shows pharmacological dissection of the VSDI signal, consistent with an example embodiment of the present invention.
FIG. 1C shows single-pixel response ($\Delta F/F$ vs. time, post-averaging and filtering; top) from the indicated region to the given stimulus train (bottom), consistent with an example embodiment of the present invention.
FIG. 1D shows the results of cross-correlation analysis and region of interest extraction, consistent with an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of processes, devices and arrangements involving imaging excitable tissue. Aspects of the present invention have been found to be particularly advantageous in applications benefiting from or involving assessment of neural activity. While the present invention is not necessarily so limited, various aspects of the invention may be appreciated through a discussion of examples using this context.

Embodiments of the present invention are directed to methods, systems and devices for assessing electrical activity of a neural region. Aspects of the invention allow for assessment of such electrical activity with high temporal and spatial precision. High-speed and high-resolution imaging devices capture data responsive to the electrical activity. Specialized processing techniques are used to assess the electrical activity by correlating time and phase information about the captured data.

In connection with various embodiments of the present invention, a neural region is targeted for assessment of neural activity. The neural region has subfields or local networks consisting of a relatively small number of neural cell groups. Image capture of a subfield is performed so as to provide sufficient detail in space and time to differentiate between polarization events (i.e., depolarization events or hyperpolarization events) of respective portions of the subfield. These portions can range from a single neuron to a small group of neurons sufficient to distinguish individual polarization events within the portions of the subfield. In a particular instance, the respective portions represent one or more captured image pixels. In one instance, the spatial detail is on the order of millimeters (e.g., sub centimeter). In another instance, the spatial detail is on the order of micrometers (e.g., sub millimeter). The temporal detail can range from around a half second to a few milliseconds or even faster.

One embodiment of the present invention involves the use of spatial and temporal correlation techniques to assess the neural activity of subfields. These techniques are designed to scale with the precision of the image capture technology allowing for use with a wide variety of current and future image capture technologies.

Embodiments of the present invention use voltage sensitive dye imaging (VSDI) to probe quantitatively the dynamics of other neural networks following the induction, diagnosis or treatment of medical states or diseases. One such embodiment uses VSDI to probe quantitatively the differences in network activity due to various factors including, but not limited to, those differences underlying psychiatric disease and treatment.

Other embodiments of the present invention use other imaging techniques, such as infrared imaging, near-infrared imaging or optical topography. Such techniques involve the capture of image data relative to the properties of blood within the neural region (e.g., hemoglobin concentrations). Activity within the neural region results in rapid changes to localized blood volume. The captured image data includes data regarding the properties of the blood within specific regions of the neural region. This data is obtained through a determination of optical absorption coefficients.

A specific embodiment of the present invention uses a VSDI process to assess correlations between stimuli and resulting electrical responses. Stimuli elicit responses from the neural network. Voltage responsive dyes allow images of the responses to be captured using an imaging device. Correlation techniques are implemented to match the data from the imaging device to the stimuli. For instance, delays are inherently present between the application of the stimuli and the capturing of the image data. Factors in the delay include, but are not limited to, propagation delay through the neural network, delay in the voltage-sensitive dye response, imaging device delays and processing delays. In a particular embodiment, the stimuli profile is compared to the image data with respect to time/phase. The comparison can be accomplished by implementing a pixel-by-pixel correlation between the stimulus and the pixel response. The pixel response can be determined as the amount of change from one frame to the next.

One embodiment of the present invention uses voltage sensitive dye imaging (VSDI) to probe quantitatively the dynamics of neural networks (e.g., hippocampal) with millisecond resolution following bidirectional affective state modulation (including both induction and treatment of depressed-like states). It has been found that a single measure of high-speed neurophysiological activity—the evoked spread of activity through the dentate gyms of the hippocampal formation, relative to that in CA1, accounts for bidirectional changes in animal behavior in a manner that is independent of the underlying mechanism of action of the affective state modulators. These high-speed imaging results define a network-level endophenotype for depression unifying disparate findings in the literature, and demonstrate a tractable approach to the understanding and treatment of neural substrates of psychiatric disease.

While much of the discussion herein is directed to VSDI and/or optical tomography, the invention is not so limited. To the contrary the various embodiments, for example, the processing and correlations techniques, are applicable to any number of different data capture techniques. For instance, the processing and correlation techniques can be applied to any data set that contains temporal and spatial information having sufficient granularity and precision.

In an example of one such an alternative embodiment, a slice of brain is obtained which includes representative samples of the prefrontal cortex, the dorsolateral prefrontal cortex, and the subgenual cingulate. This block of tissue is treated with a calcium dye. Various calcium dyes are able to resolve ion flux on a cellular scale with microsecond precision. Using such dyes, the activity of these regions can be used to assess the neural activity of various regions and their interconnections. For example, an assessment could be made as to whether the dorsolateral prefrontal cortex has a direct correlation with the activity of the prefrontal cortex, and inverse relationship with the activity of the subgenual cingulate cells. In the case of depression, this may reach a steady state in which the subgenual cingulate is relatively overactive as compared with the prefrontal cortex. In the context of this experimental paradigm, candidate drugs may be tried with respect to their differential effect on these regions within the sample. Ideal drugs for example might serve single targeted neurophysiological roles, without creating additional neurophysiological effects which are competitive to the therapeutic goal. For example, a drug which succeeds in lowering activity levels in the subgenual cingulate without lowering activity in the prefrontal cortex as well may be preferable to one which attempts to lower activity generically in both. Also in the context of such an embodiment, ideal locations for neuromodulation of specific sites within the circuit may be identified, with and without the benefit of synergistic medications.

Readout or image capture of the physiological activity of the neural network can be accomplished by a variety of techniques including calcium imaging, biochemical imaging and infrared imaging. PET and fMRI may also be applicable, albeit at lower spatial and temporal resolutions.

Stimulating the circuit may be accomplished with a variety of means that influence cellular activity, including application of drugs, magnetic fields, electrical current, optical (including opto-genetic) stimulation, ultrasound thermal and radiation methods as are known in the art.

Figure 7:
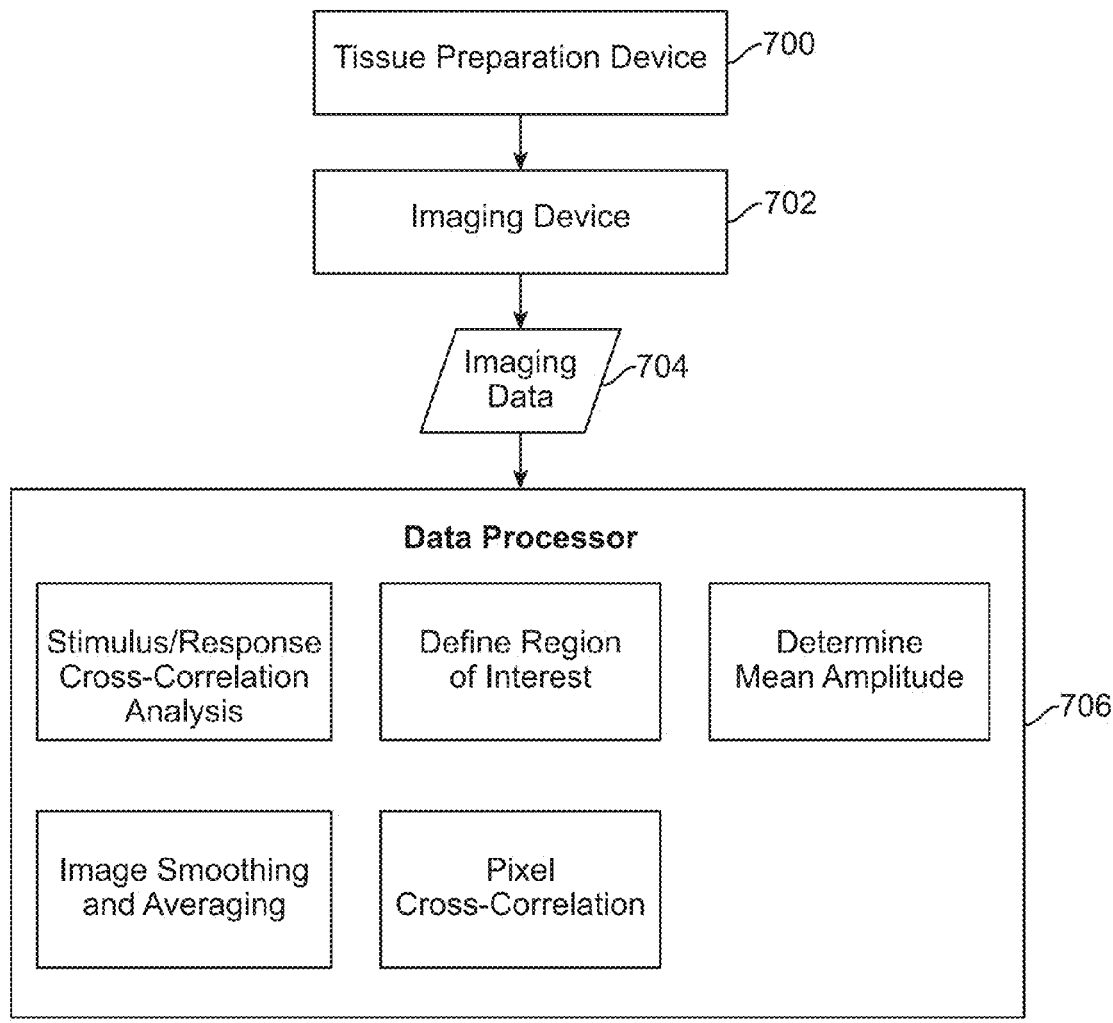
FIG. 7 shows an example system for determining characteristics of neuronal networks, according to an example embodiment of the present invention.

FIG. 7 shows an example system for determining characteristics of neuronal networks, according to an example embodiment of the present invention. Tissue preparation device 700 includes the preparation of the neuronal network for various imaging techniques, such as staining the tissue with voltage sensitive dye. In one instance, tissue preparation device 700 includes a device to stimulate the appropriate portion of the neuronal network. This can be accomplished using electrodes, light (e.g., by modifying the target network to react to light using optically responsive channels or pumps) and/or similar techniques, as has been recently published with reference to DBS applications. Image device 702 records the resulting signals. In one instance, image device 702 is a high speed camera capable of capturing signals derived from action potentials of the neuronal network. Imaging data 704 is received from image device 702 by data processor 706. The data is processed to filter unwanted signals, determine the target area and to calculate the amount of activity. As discussed in more detail herein, the process can include a number of steps including, but not limited to, cross-correlation analysis between the stimulus and the response, image smoothing and averaging, definition of the region of interest, pixel to pixel cross correlation and calculation of the mean amplitude of the region of interest.

Depending on the readout source, data may be captured for example with a CCD camera, or as a digital matrix of sensor readings obtained from a sensor grid, or serially positioned sensors. Processing resultant readout data by correlating activity level of cell types may be accomplished with computer software, for image analysis applications such as Image J (U.S. National Institutes of Health, Image J consortium). Providing processed correlation results to the user may be provided through screen displays, printed and transmitted data.

Figure 8:
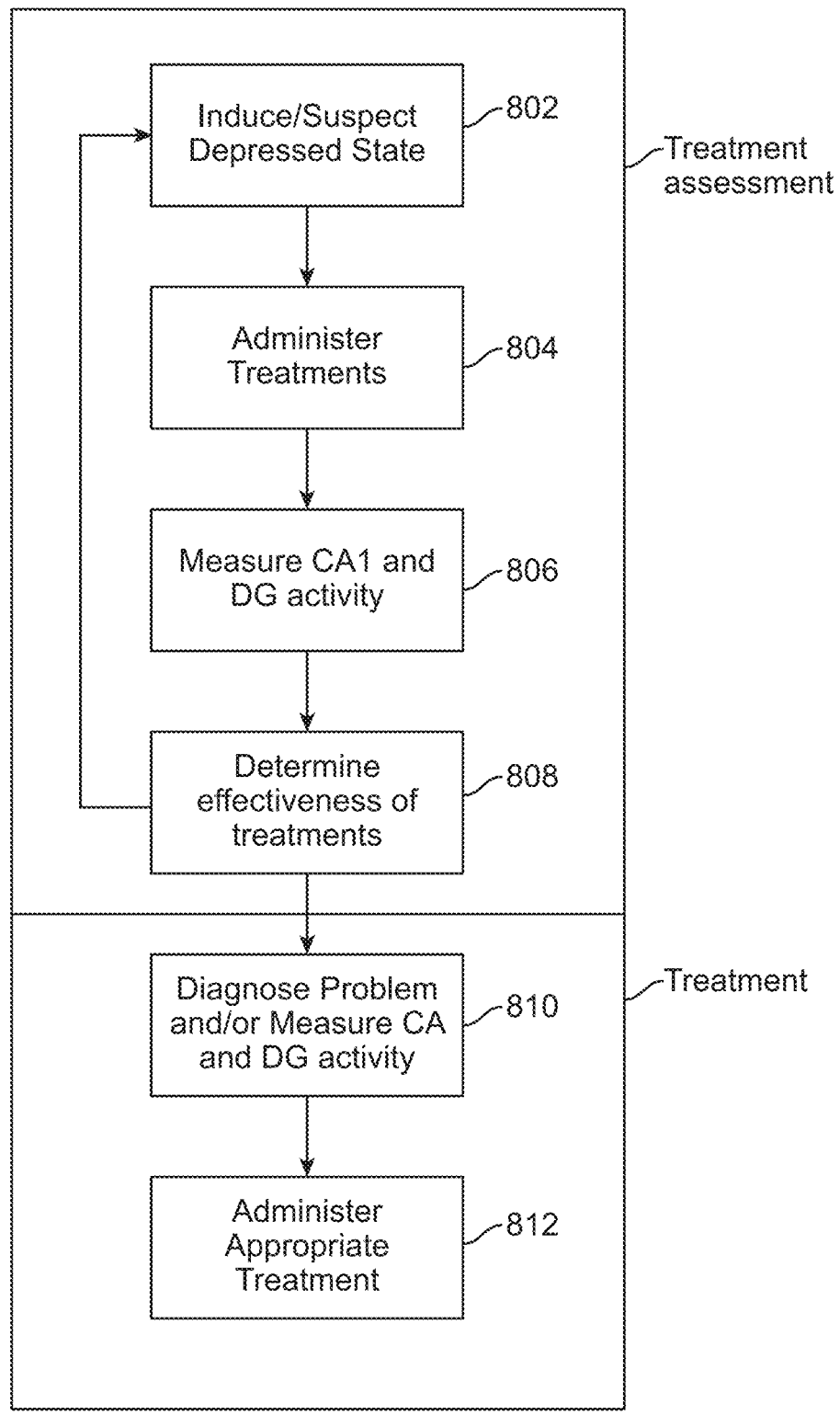
FIG. 8 shows a flow diagram of a process for treatment of depressed states in patients, according to an example embodiment of the present invention.

FIG. 8 shows a flow diagram of a process for treatment of depressed states in patients, according to an example embodiment of the present invention. At block 802 the depressed state is induced on an animal, such as a rat. Alternatively, the depressed state could be diagnosed rather than induced. This is particularly useful for modifying this portion of the process to be used with human patients. Treatments (e.g., drugs, dietary changes, environmental changes) are administered to the depressed state animals at block 804. In one instance, the use of control groups and statistical techniques can be used to bolster the validity of any results obtained. At block 806, the amount of activity in the DG and CA1 areas of the brain are measured and quantified. The results of the treatments can then be determined at block 808. This portion of the process can then be repeated for different treatments and different depressed states. Future patients can be diagnosed with a similar depressed state at block 810. This can be accomplished through various techniques, such as identifying the depressed state through symptoms and by measuring the activity of the DG and CA1 areas of the brain. Using the determination from block 808 the appropriate treatment can then be administered.

The various methods and systems discussed herein (including those discussed in connection with the flow diagram of FIG. 8) can be applied to a number of applications other than those related to either depression or the DG and CA1 subfields. A few example disorders for which treatments can be screened include, but are not limited to, Alzheimer's disease, mild cognitive impairment, autism, bipolar disorder, schizophrenia, and Down Syndrome. Other instances involve the use of the invention to assess areas of the human nervous system including, but not limited to, the neocortex, archicortex, paleocortex, cerebellum, medulla or spinal cord. Within the hippocampus (a structure on the temporal lobe of the neocortex) for example, pertinent cellular areas involved with a specific circuit include the dentate gyns, the CA1 field, the CA3 fields. Various examples include, but are not limited to, the upstream and downstream connections to the hippocampus (e.g., the hypothalamus, frontal cortex, enthorhinal cortex, cingulate cortex, mammillary bodies, septum, bed nucleus of stria terminalis, amygdala, and nucleus accumbens). Other embodiments target excitable cells other than those of the brain, such as the nervous system or cardiac conduction system (e.g., sinoatrial node, atrioventricular (AV) node, bundle of His; bundle branches; internodal tracts, anterior-superior and posterior-inferior divisions of the left bundle and the Purkinje network).

In order to assess the network activity a number of different methods can be used to evoke a response in the target neural region. A first example involves applying direct electrical stimulation to a portion of the network. This can be accomplished using, for example, patch clamping or other electrical probe devices and methods. Another example involves the use of various electromagnetic (EM) waves to evoke the desired response. Various different EM wave sources are possible depending upon the type of EM wave. A first example includes optical (visible or near-visible) EM waves from a number of sources, such as light-emitting-diodes (LEDs) or lasers. Another example of EM-type stimulus includes gamma rays or X-rays. Additionally, a response can be evoked using physical stimulus, such as physical perturbation provided by ultra-sound. Ultra-sound can also be used to evoke a response by heating the target neural region. Yet another mechanism for evoking a response includes the use of a pharmacological or chemical agent to affect the firing rate of the neural region.

For applications involving a live subject, in addition to the stimulus discussed above, a response can be evoked by providing any number of external stimuli to the subject including, but not limited to, physical, mental and chemical stimuli.

A specific embodiment of the present invention can also be implemented by relying upon intrinsic neural activity. In this context, evoking a response involves providing conditions for the neural network that are conducive to producing the intrinsic neural activity. For example, the cardiac conduction system includes the intrinsic firing of both the SA and AV nodes. Intrinsic network activity from either or both of these nodes can be assessed by providing proper conditions for the neural networks. Additionally, the effects of various treatments (e.g., drugs or otherwise) on the intrinsic network activity can also be assessed by first applying the treatments and assessing the resulting network activity. Another possible implementation for intrinsic neural activity is to correlate interdependencies between areas within a subfield or between different subfields.

Figure 15A:
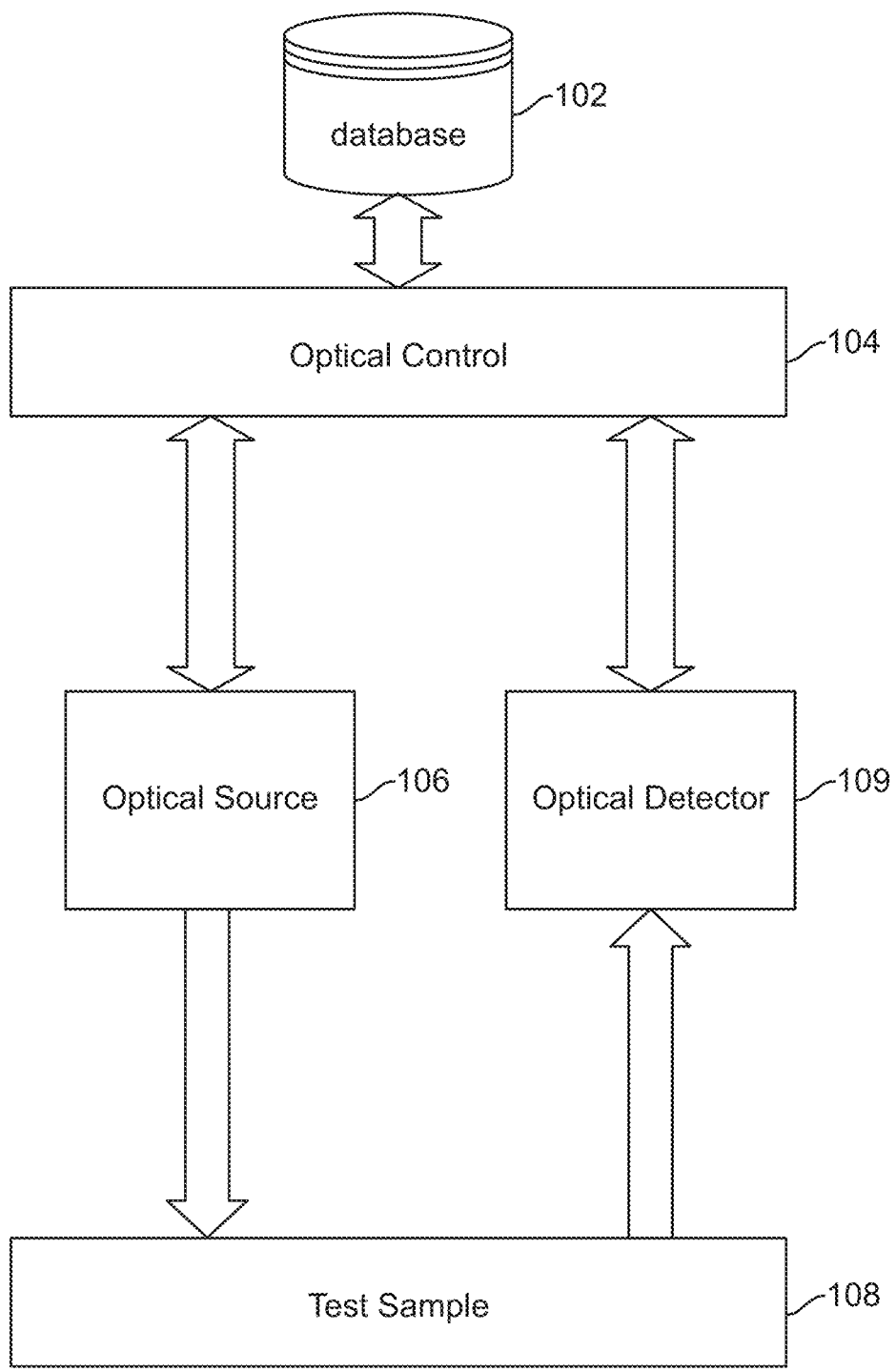
FIG. 15A shows a block diagram of a system for optical drug screening, according to an example embodiment of the present invention.

FIG. 15A shows a basic block diagram of a system for screening for neural network affecting drugs or treatments, according to an embodiment of the invention. Optical control 104 communicates with database 102, optical source 106 and optical detector 109. Optical source 106 provides optical stimulus to test sample 108. Test sample 108 includes the drug under test, neural cells that have optically responsive ion channels, and a voltage/ion indicator. Alternatively test sample 108 does not include a drug, but rather the neural cells have been treated in some other manner.

Test sample 108 includes a neural network that is under test. In a specific example, the neural network is representative of one or more specific subfields of the brain. The effects of a particular drug or treatment may be monitored for more than just average activity over time. Using an embodiment of the present invention, the effect of the treatment with respect to specific activity patterns within a subfield can be monitored and assessed.

In one instance, the indicator fluoresces in response to light from optical source 106. Optical control 104 may also include a reconfigurable readout, so that as different light-activated membrane potential switches (LAMPS) and different light-emitting indicators of cellular activity (LEIAs) are used, the same control system can be readily adapted to each paradigm. Optical detector 109 produces a signal responsive to such florescence, and optical control 104 receives the produced signal. The optical control 104 stores data obtained from the signal in database 102. The information stored includes spatial and temporal data regarding the electrical activity of the test samples 108. Other information may include factors such as the intensity, duration and wavelength of the detected light. In a particular instance, the stored data can be compared against baseline data, where the baseline data corresponds to data recorded prior to the introduction of the drug to the test sample 108. In another instance, optical source 106 may vary the intensity, duration or other parameters related to the control of optical source 106. These and other parameters may be stored in database 102. These parameters are then used to assess the network activity.

It should be apparent that optical source 106 may be implemented using a single light source, such as a light-emitting diode (LED), or using several light sources. Similarly, optical detector 109 may use one or more detectors and database 102 may be implemented using any number of suitable storage devices.

FIG. 15B shows a system diagram of a large-format, quasi-automated system for drug screening in accordance with a specific embodiment of the invention. Control device 101 (e.g., a computer or control logic) controls various processes, and serves as the central point of system input/output functions. The environment may be maintained at an appropriate temperature, humidity, carbon dioxide level and ambient light level within the walls of the climate control chamber 105, with the help of one or more sensors 114 (e.g., thermostat, carbon dioxide sensor and humidity sensor), carbon dioxide and humidifier apparatus 112, and heater 110. Multi-well tray 141 contains test wells 140 for holding cultured cells, drugs, and other ingredients needed for each test. Tray 141 rests upon X-Y-Z table 125, the movement of which is carried out by table actuators 120, under control of computer 101. Xenon lamp 155 emits high-intensity white light 156, which is passed through color filter 160. In the case that ChR2 is used for stimulating the cells within wells 140, color filter 160 is blue, causing blue light 161 to exit the filter, and strike dichroic mirror 170. Blue light 161 then passes upward, through microscope objective lens apparatus 130, and through the bottom of transparent tray 141. In this fashion, the contents of wells 140, with their transparent undersides, are illuminated. When a separate wavelength of light is required to stimulate a fluorescent light-emitting indicator of cellular activity, a filter of the appropriate specification may be substituted for the previous filter 160, causing light of the proper wavelength for this latter task to be piped toward well 140. If the cells within well 140 have been light-sensitized, and if the drug being tested in each of these wells does not suppress the process, a light-emitting indicator of cellular activity (LEIA), which has also been added to each well or expressed by the cells via genetic modification, will emit light in accordance with the voltage change caused by the effect of the light. This second wavelength of light, which may be much smaller in magnitude than the stimulation light, is collected by microscope turret 135, will also be passed through dichroic mirror 175, onto the lens of (CCD) camera 180.

Dichroic mirror 170 allows for upward reflection of both the wavelength required to stimulate the optical gating of the membrane (e.g., blue for ChR2), and the wavelength required by any LEIA used (e.g., ultraviolet for FURA-2). This dichroic mirror may be arranged to allow passage of the output spectrum of the LEIA (e.g., blue-green for FURA-2) with minimal reflection or absorption.

For further details regarding drug screening processes, systems and devices, including those directed to a high-throughput screening environment, such as array-based optical screening system, reference can be made to U.S. Patent Application No. 60/996,116, to Zhang et al., filed on Aug. 10, 2007 and entitled "Cell Line for Optically-Based Screening of Ion Channel Modulators".

Figures 9A, 9B:
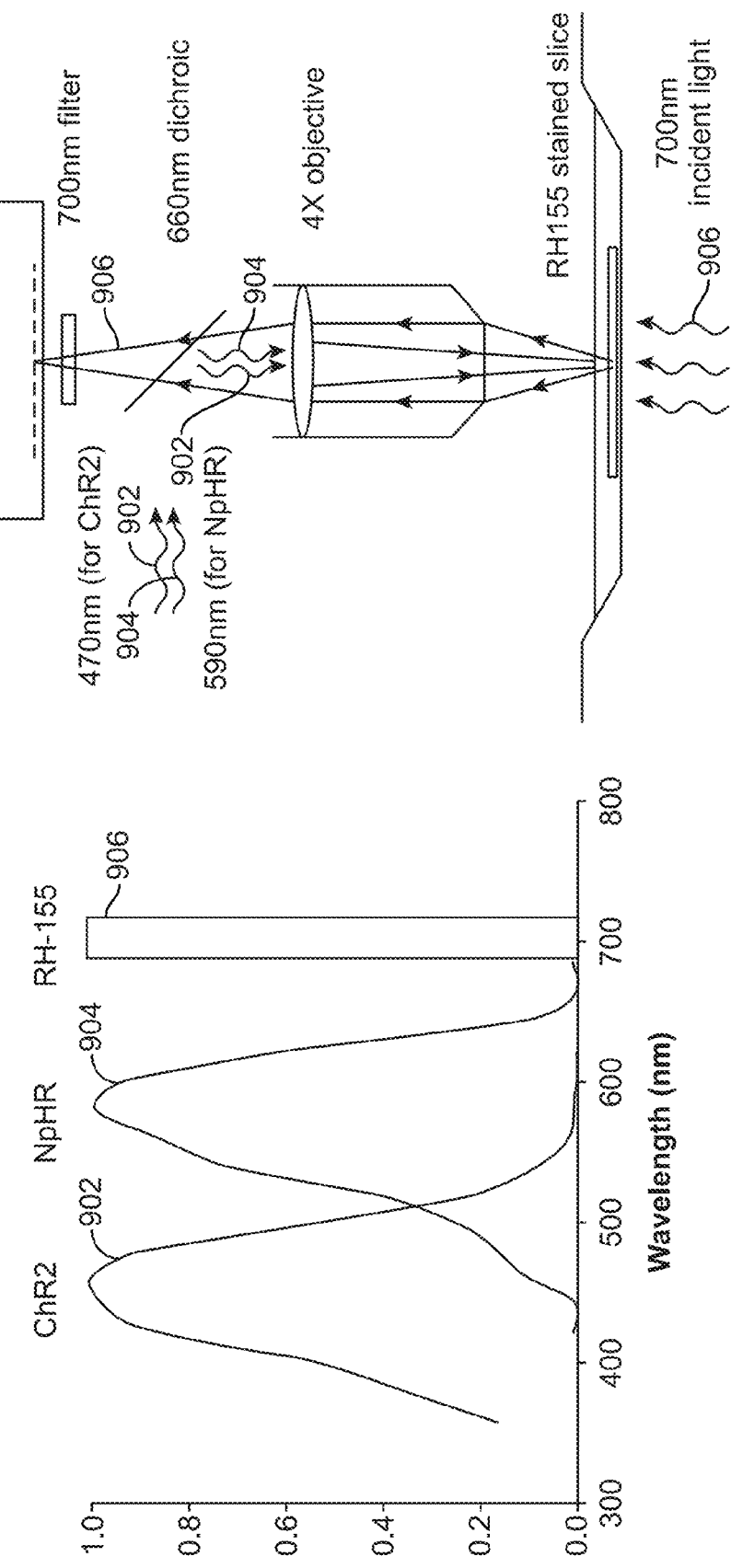
FIG. 9A shows a wavelength diagram for use in a VSDI imaging process, according to an example embodiment of the present invention.
FIG. 9B shows an imaging apparatus for use in a VSDI imaging process, according to an example embodiment of the present invention.

FIG. 9A shows a wavelength diagram for use in a VSDI imaging process, according to an example embodiment of the present invention. FIG. 9B shows an imaging apparatus for use in a VSDI imaging process, according to an example embodiment of the present invention. A specific embodiment of the present invention uses light-activated channel/pump proteins, such as channel-rhodopsins (ChR2) and halorhodopsins (NpHR), to stimulate the cell to be imaged. The wavelength of light 902 that ChR2 responds strongly to is around 470 nm. The wavelength of light 904 that NpHR responds strongly to is around 590 nm. An example VSDI (RH-155) responds strongly to light 906 having a wavelength of around 700 nm. FIG. 9B shows that light 902 and 904 can be directed at target cells. The difference in wavelengths is useful for allowing individual control of the specific light-activated channel/pump proteins (e.g., one of ChR2 or NpHR). A dichroic mirror can be used to direct light 902 and 904 toward the target cells. Light from the VSDI is captured by a camera and processed accordingly. This all-optical stimulation/inhibition/imaging process can be particularly useful for, among other things, precise temporal and spatially controlled stimulation and for avoiding disadvantages associated with electrode-based stimulus or patch-clamp techniques. For further details regarding such all-optical systems reference can be made to "Integration of Light-Controlled Neuronal Firing and Fast Circuit Imaging" by Airan, et al. (*Current Opinion in Neurobiology* 2007, 17:587-592), which is fully incorporated herein by reference.

The hippocampus is an example target for various embodiments of the invention, as it is not only a central component of limbic neural circuitry implicated in depression and drug response, but also the gateway through which multimodal sensory information is stored and flows to the limbic system. Models of hippocampal function from the memory literature can be used as a framework for understanding how the hippocampus may mediate affective responses. These models assign fundamentally different roles to the associative (e.g., dentate gyrus or DG) and output (CA1) subfields of the hippocampal formation in spatial and temporal memory processing. For example, the CA1 region is often conceptualized as a comparator of signals received directly from the cortex, to signals received from DG (by way of CA3), that then outputs this difference or "error" signal to downstream cortical and subcortical structures. The DG and CA1 local networks not only operate very differently, but neurogenesis occurs only in the DG; moreover, neuromodulators and stress hormones each can yield distinct effects on the DG and CA1 subfields. In light of these differences, the disparate clinical findings regarding hypoactivity or hyperactivity of the hippocampal formation in depression could in principle be reconciled with technology capable of separately resolving electrical activity of the associative (e.g., DG) and output (CA1) local circuits in behaviorally relevant paradigms. An example application of VSDI imaging consistent with an embodiment of the present invention is used to address such disparate clinical findings. While the invention is not so limited, the discussion of such a specific application can be useful to an understanding of the present invention.

In probing the neurobiology of psychiatric disorders, rodent models have proven useful in isolating key features that may underlie disease etiology. Models of depression include paradigms based on stress, learned helplessness, neurological lesion, and/or genetic manipulation. In particular, the chronic mild stress (CMS) paradigm has excellent predictive, face and constructs validities, models core symptoms, and is considered to be an ethologically relevant model of depression. Although molecular, synaptic, cellular, and anatomic markers have been linked to depression or antidepressants in several of these animal models of disease, a neurophysiological endophenotype of depression has yet to be identified that captures relevant changes in network activity with high spatiotemporal resolution.

Applications of the present invention implement VSDI technology as a powerful, quantitative tool to probe the alterations in network activity to determine their contributions to neuropsychiatric disease. For example, given the primary role of the hippocampus in depression and its treatment, VSDI was used to observe hippocampal activity directly with high spatial and temporal resolution in rodent models of depression and antidepressant treatment. The parameters of hippocampal activity measured by VSDI reliably predict behavioral performance on a forced swim test following combinations of CMS and chronic antidepressant treatment. Specifically, CMS significantly reduces activity in the DG and increases activity in CA1; moreover, chronic antidepressant treatment induces opposite effects, confirming the initial hypotheses. Together, these results identify the activity of the DG relative to CA1 as a neurophysiological endophenotype of depression that spans responses to distinct classes of antidepressants, combinations of stress exposure and antidepressant treatment, and multiple mechanisms of action on the cellular level. The DG-CA1 relative activity, a subfield-resolved measure of high-speed hippocampal electrical activity, unifies contradictory and disparate findings in the field and may represent a common pathway through which mechanistically diverse processes contribute to depression and its treatment.

To use high-speed VSDI to explore neuronal network activity changes in psychiatric disease models, experimental analysis methods were developed to extract reliable quantitative features from the imaging data across animals. A specific implementation of one embodiment of the present invention was used to probe the DG-CA1 activity in depressed mice. A description of the figures related to this implementation follows, with specific details of the implementation provided thereafter.

FIG. 1 shows voltage sensitive dye imaging (VSDI) of such hippocampal network activity. FIG. 1A shows representative filmstrip acquired using VSDI. Times indicated are relative to a single pulse of stimulus current applied to the perforant path. Warmer colors indicate greater activity ($\Delta F/F$) in the corresponding pixel. Data represents the average of four individual sweeps; traces were low-pass filtered (0.5 kHz cutoff), and frames were spatially filtered with a 5×5 Gaussian spatial average.

FIG. 1B shows pharmacological dissection of the VSDI signal. The signal is initiated by excitatory synaptic transmission as it is greatly reduced with NBQX application (10 μM) and abolished with concurrent D-AP5 application (25 μM). GABAzine (2004) and TTX (1 μM) were applied subsequently to confirm signal extinction.

FIG. 1C shows single-pixel response ($\Delta F/F$ vs. time, post-averaging and filtering; top) from the indicated region to the given stimulus train (bottom).

FIG. 1D shows the results of cross-correlation analysis and region of interest extraction. The phase (top left) and amplitude (top right) of maximal correlation between the stimulus and response at each pixel is also shown. The region responding to the stimulus was extracted computationally based on similar phase values of responding pixels (bottom).

Figure 2:
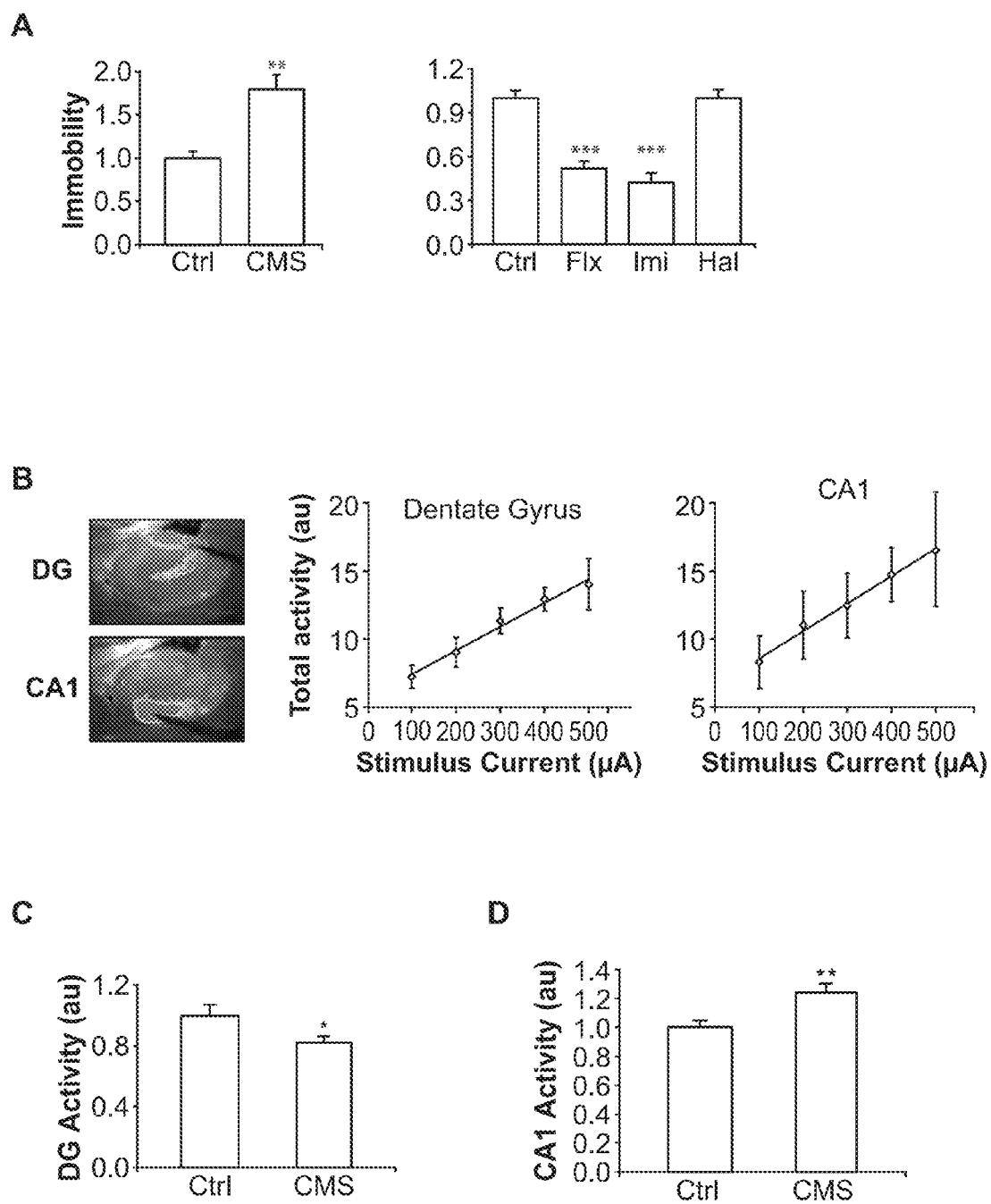
FIG. 2A shows results of a chronic mild stress (CMS) induced ethologically relevant depressed-like state and animals treated chronically with the indicated drug condition to model antidepressant and antipsychotic treatment, consistent with an example embodiment of the present invention.
FIG. 2B shows linear and quantitative response of the VSDI total activity signal to applied stimulus current in both the dentate gyms (DG) and Cornu Ammonis region CA1, consistent with an example embodiment of the present invention.
FIG. 2C shows evoked DG activity was significantly decreased in CMS-treated animals, consistent with an example embodiment of the present invention.
FIG. 2D shows evoked CA1 activity was significantly increased in CMS-treated animals, consistent with an example embodiment of the present invention.
FIG. 2E shows relative activity between DG and CA1 activity, calculated for each slice and averaged together for each animal, consistent with an example embodiment of the present invention.
FIG. 2F shows evoked DG activity was significantly increased in antidepressant, but not haloperidol, treated animals, consistent with an example embodiment of the present invention.
FIG. 2G shows evoked CA1 activity was decreased in antidepressant, but not haloperidol, treated animals, consistent with an example embodiment of the present invention.
FIG. 2H shows relative activity between DG and CA1 activity calculated for each slice and averaged together for each animal, consistent with an example embodiment of the present invention.
Figure 2:
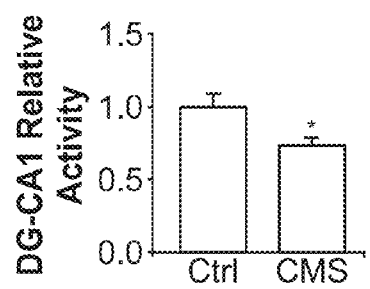
Figure 2:
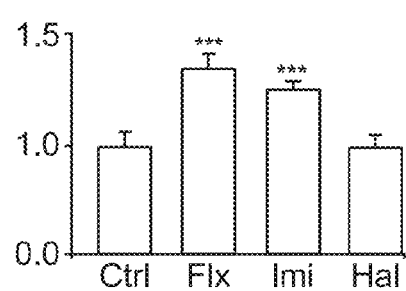
Figure 2:
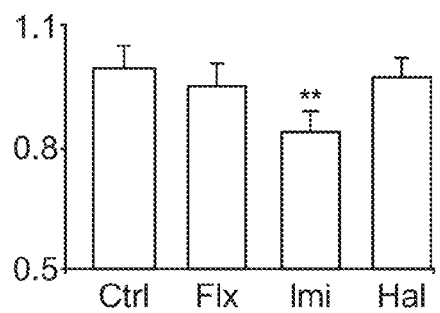
Figure 2:
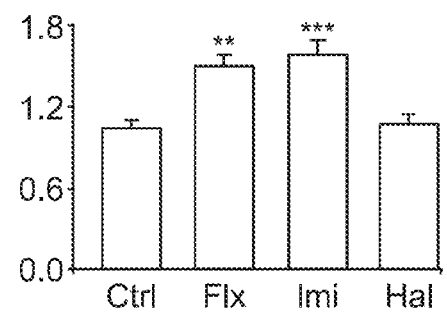

FIG. 2 shows bi-directionally modified hippocampal network dynamics in depressed-like states and antidepressant treatment. FIG. 2A shows a chronic mild stress (CMS) induced ethologically relevant depressed-like state (left). A separate group of animals was treated chronically with the indicated drug condition to model antidepressant and antipsychotic treatment (right, Ctrl—control, FIX—fluoxetine, Imi—imipramine, Hal—haloperidol). After completion of either protocol, a 5-minute forced swim test (FST) was employed to probe behavior, and voltage sensitive dye imaging (VSDI) employed to measure network activity in acute hippocampal slices prepared from the same animals. All assays were performed blind to treatment group and presented data are normalized by the respective control means. CMS treated animals displayed significantly increased immobility time relative to controls, confirming depression-like behavior (left, student's t-test,  $p<0.01$, n=6 animals per group). Fluoxetine and imipramine animals show a decreased immobility time, confirming an antidepressant effect, and no such effects were observed in haloperidol treated animals (right, ANOVA, $F_{3,22}=29.46$, * $p<0.001$, n=5-6 animals per group).

FIG. 2B shows linear and quantitative response of the VSDI total activity signal (mean signal amplitude times region of interest area) to applied stimulus current in both the DG (top left and middle, n=7 slices, $R^2=0.9855$) and CA1 (bottom left and right, n=5 slices, $R^2=0.9926$). Left: Sample frames from imaging of DG and CA1 responses, processed as in FIG. 1A.

FIG. 2C shows evoked DG activity was significantly decreased in CMS-treated animals (student's t-test, * $p<0.05$, n=65 (control) and n=72 (CMS) evoked slice responses).

FIG. 2D shows evoked CA1 activity was significantly increased in CMS-treated animals (left, student's t-test, ** $p<0.01$, n=79 (control) and n=75 (CMS) evoked slice responses).

FIG. 2E shows relative activity between DG and CA1 activity, calculated for each slice and averaged together for each animal. Significant reduction was seen in CMS (student's t-test, * $p<0.05$, n=6 animals per group).

FIG. 2F shows evoked DG activity was significantly increased in antidepressant, but not haloperidol, treated animals (ANOVA, $F_{3,267}=34.75$, *** $p<0.001$, n=60-72 evoked slice responses per group).

FIG. 2G shows evoked CA1 activity was decreased in antidepressant, but not haloperidol, treated animals (ANOVA, $F_{3,270}=5.173$, ** $p<0.01$, n=59-72 evoked slice responses per group).

FIG. 2H shows relative activity between DG and CA1 activity calculated for each slice and averaged together for each animal. Significant increases were seen in both antidepressant treatment groups, but absent in haloperidol group (ANOVA, $F_{3,22}=12.74$,  $p<0.01$, * $p<0.001$), corresponding well to observed behavior in FIG. 2A.

Figure 3:
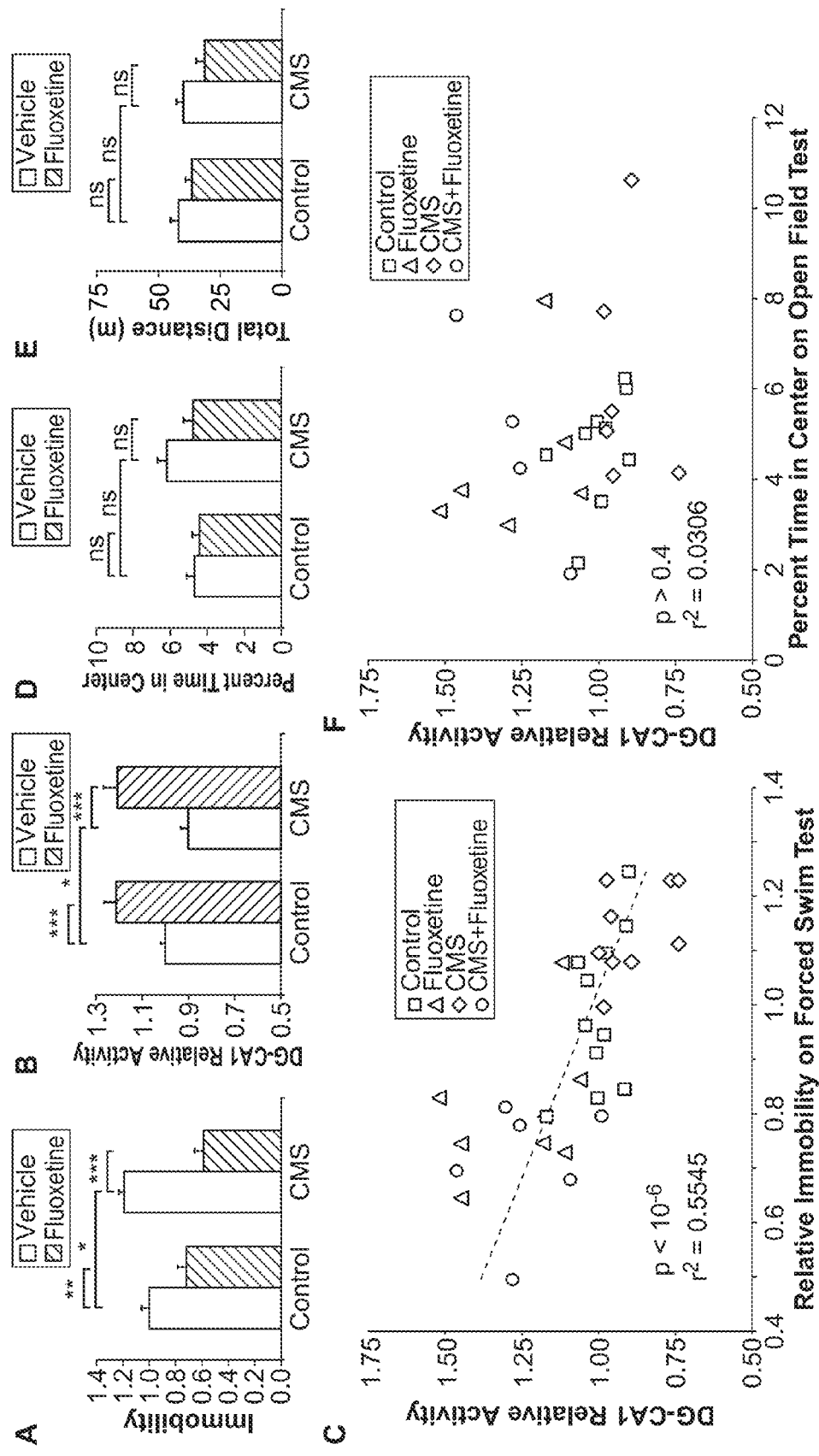
FIG. 3A shows immobility times of CMS treated animals relative to controls, and fluoxetine treatment in both control and CMS groups, consistent with an example embodiment of the present invention.
FIG. 3B shows activity of DG relative to CA1 in CMS-treated animals and fluoxetine treated animals in both CMS and control groups, consistent with an example embodiment of the present invention.
FIG. 3C shows linear regression of the DG-CA1 relative activity against the forced swim test (FST) scores for each individual animal, consistent with an example embodiment of the present invention.
FIG. 3D shows percent time in center on the open field test (OFT) for treatment groups, consistent with an example embodiment of the present invention.
FIG. 3E shows that no differences in total distance on the OFT were observed for any treatment group indicating lack of motility-related confounds, consistent with an example embodiment of the present invention.
FIG. 3F shows that linear regression of the DG-CA1 relative activity against the OFT scores for each individual animal, consistent with an example embodiment of the present invention.

FIG. 3 shows that high speed network-dynamics measurements correlate with antidepressant treatment of depressed-like behavioral states. To develop the data depicted by FIG. 3, chronic mild stress (CMS) was used for five weeks to induce a depressed-like state and fluoxetine was administered during the final two weeks of the stress protocol. After completion of this protocol, a 5-minute forced swim test (FST) and open field test (OFT) were employed to probe behavior, and voltage sensitive dye imaging (VSDI) was employed to measure network activity in acute hippocampal slices from the same animals. All assays were performed blind to treatment group and FST and VSDI data are presented normalized to the control mean.

FIG. 3A shows that CMS treated animals displayed significantly increased immobility time relative to controls, and fluoxetine treatment decreased immobility in both control and CMS groups (ANOVA, $F_{3,34}$=19.24, * p<0.05,  p<0.01, * p<0.001, n=8-12 animals per group).

FIG. 3B shows that the activity of DG relative to CA1 was significantly decreased in CMS-treated animals and fluoxetine treatment significantly increased this statistic in both CMS and control groups (ANOVA, $F_{3,34}$=16.17, * p<0.05, *** p<0.001, n=6-12 animals per group).

FIG. 3C shows linear regression of the DG-CA1 relative activity against the FST scores for each individual animal ($r^2$=0.5545, p<$10^{-6}$, n=35 individual animals) demonstrating that the measured network activity accounts for more than half of the variation in FST scores across groups.

FIG. 3D shows that no differences in percent time in center on the OFT were observed for any treatment group indicating lack of anxiety-related effects of treatment (ANOVA, $F_{3,24}$=1.021, P>0.05, n=4-9 animals per group).

FIG. 3E shows that no differences in total distance on the OFT were observed for any treatment group indicating lack of motility-related confounds (ANOVA, $F_{3,20}$=1.776, P>0.05, n=4-9 animals per group).

FIG. 3F shows that linear regression of the DG-CA1 relative activity against the OFT scores for each individual animal ($r^2$=0.0306, p>0.4, n=25 individual animals) demonstrating that the network activity measure does not correlate with anxiety-related behavior.

Figure 4:
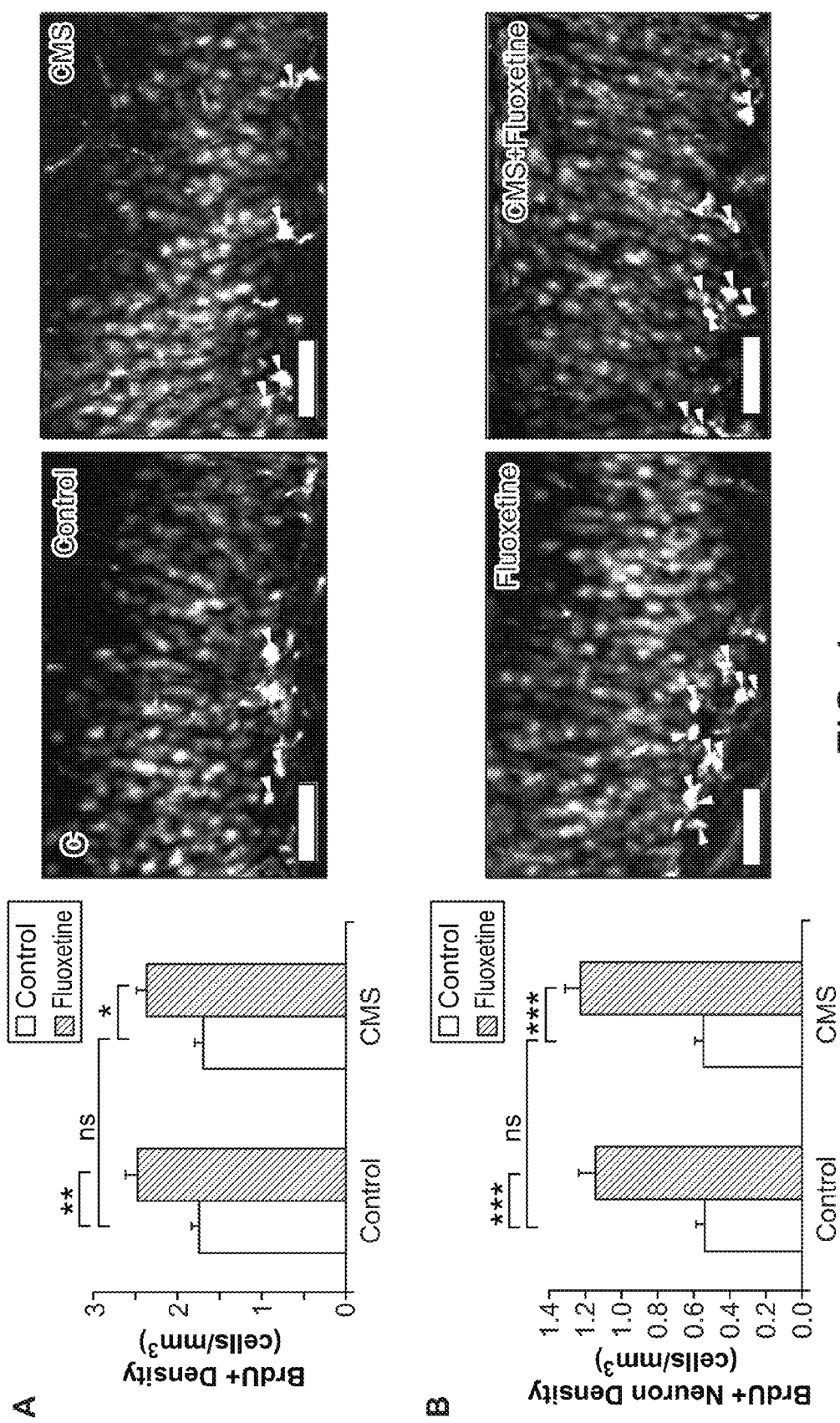
FIG. 4A shows unbiased stereological determination of BrdU+ cell density in the ventral hippocampus, consistent with an example embodiment of the present invention.
FIG. 4B shows BrdU+ neuron density, consistent with an example embodiment of the present invention.
FIG. 4C shows representative confocal images of the DG labeled for BrdU, the mature neuronal marker NeuN, and the immature neuronal marker Dcx, consistent with an example embodiment of the present invention.

FIG. 4 shows contrasting effects of antidepressant treatment and chronic mild stress (CMS) on hippocampal neurogenesis.

FIG. 4A shows that unbiased stereological determination of BrdU+ cell density in the ventral hippocampus from the same animals represented in FIG. 3 shows an increased number of new cells with fluoxetine treatment but no effect of CMS (ANOVA, $F_{3,16}$=10.01, n=3-5 animals per group, * p<0.05, ** p<0.01). BrdU (50 mg/kg/day) was administered daily during the second week of fluoxetine or vehicle.

FIG. 4B shows that phenotyping of BrdU+ cells for neuronal markers in the ventral hippocampus results in an increased number of new neurons with fluoxetine treatment but has no effect of CMS (ANOVA, $F_{3,15}$=20.37, n=3-5 animals per group, *** p<0.001).

FIG. 4C shows that representative confocal images of the DG labeled for BrdU, the mature neuronal marker NeuN, and the immature neuronal marker Dcx. Arrowheads indicate BrdU+ neurons.

Figure 5:
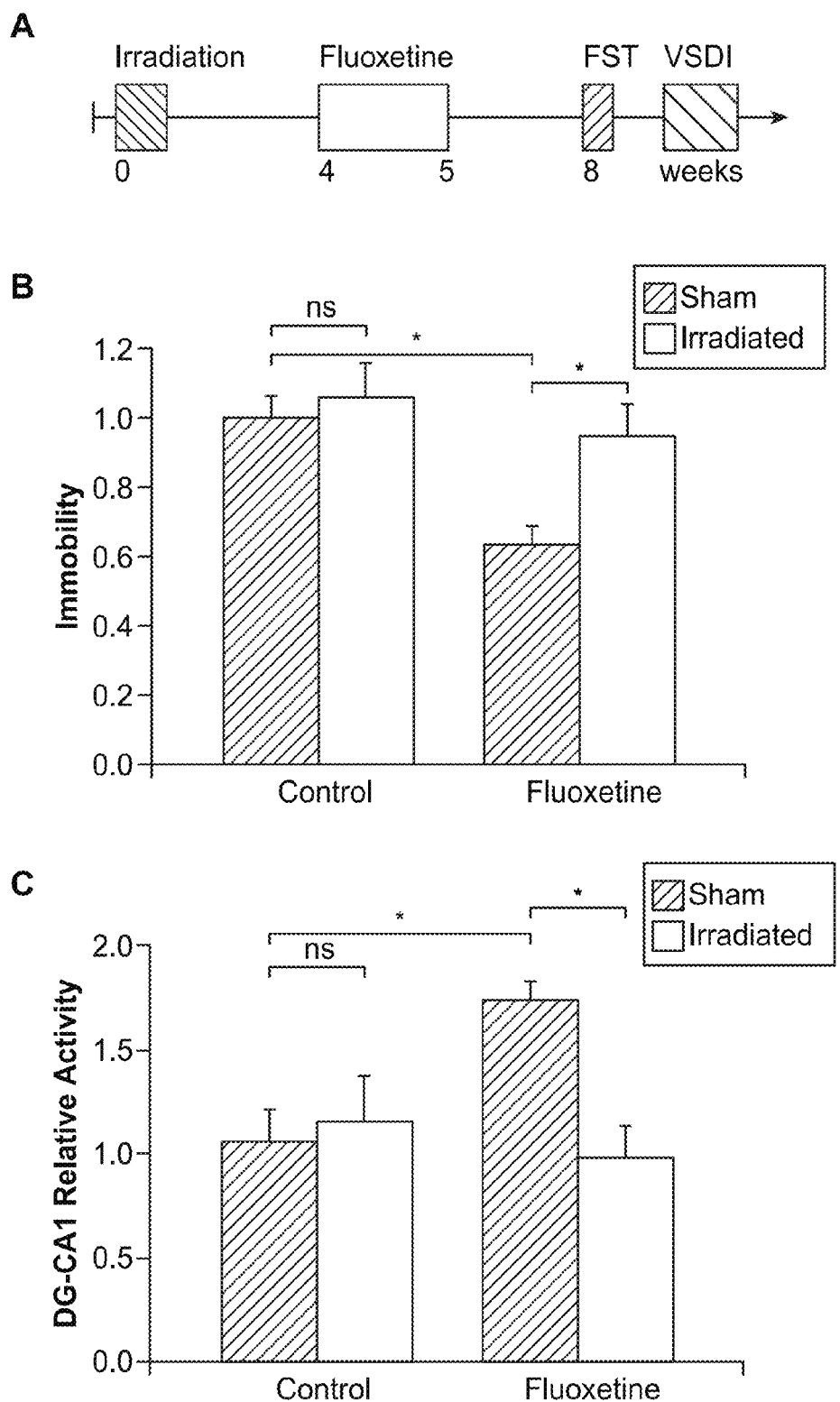
FIG. 5A shows a timeline for various steps in the imaging process, consistent with an example embodiment of the present invention.
FIG. 5B shows fluoxetine-treated animals immobility times, consistent with an example embodiment of the present invention.
FIG. 5C shows DG-CA1 relative activity with fluoxetine treatment, consistent with an example embodiment of the present invention.
FIG. 5D shows the number of total BrdU+ cells per hippocampus, consistent with an example embodiment of the present invention.
FIG. 5E shows the number of BrdU+ cells, consistent with an example embodiment of the present invention.
FIG. 5F shows the number of doublecortin (Dcx) cells, consistent with an example embodiment of the present invention.
FIG. 5G shows representative confocal images of the DG labeled for BrdU, the mature neuronal marker NeuN, and the astrocytic marker GFAP, consistent with an example embodiment of the present invention.
Figure 5:
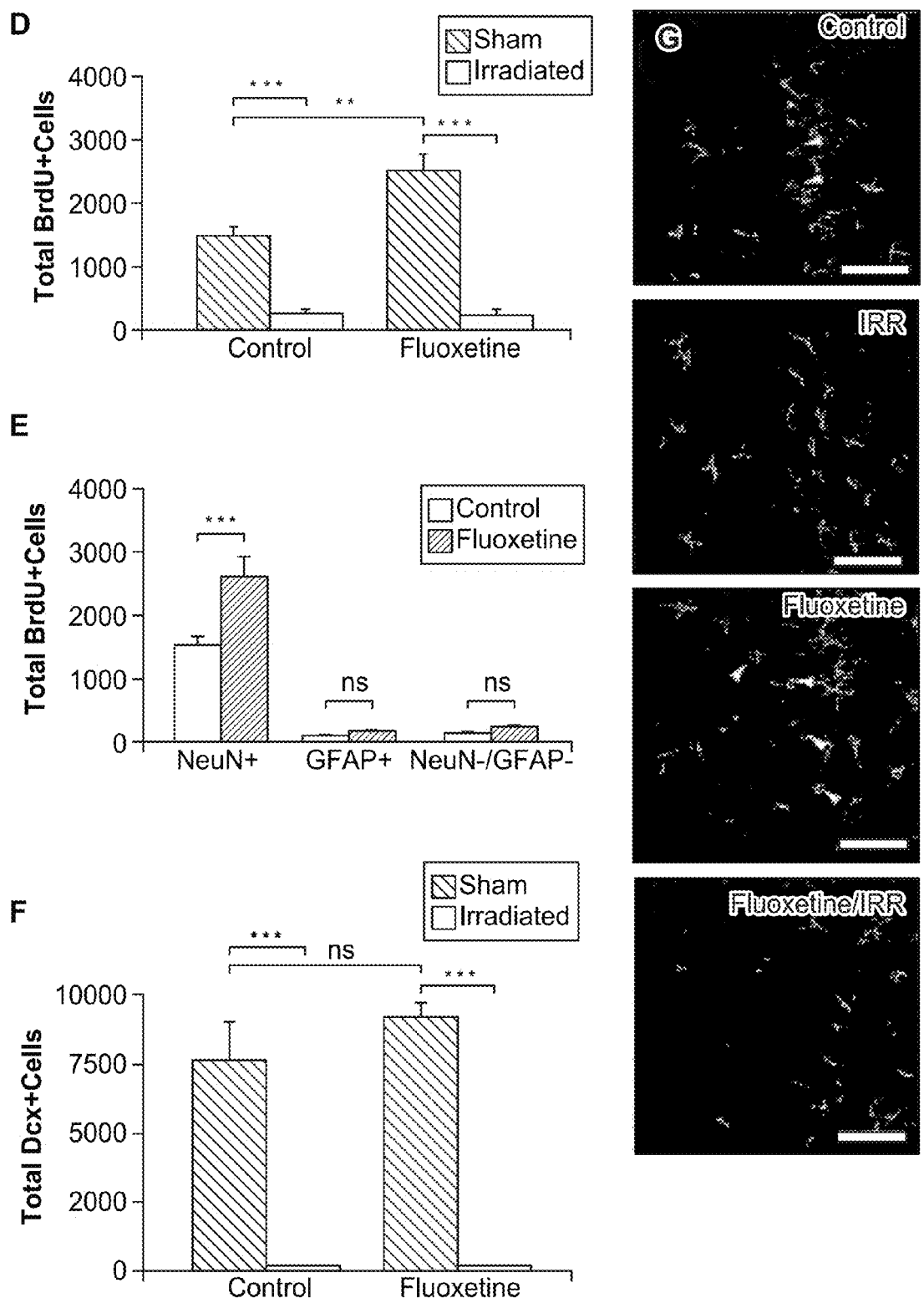

FIG. 5 shows that neurogenesis is necessary for the network dynamics and behavioral effects of antidepressant treatment.

FIG. 5A is a timeline showing various steps in the imaging process. After an irradiation protocol (sham or 10 Gy/day over 2 days) designed to ablate hippocampal neurogenesis, female rats were administered 20 mg/kg/day of fluoxetine or vehicle, followed by a 3 week delay for drug clearance and newborn neuron incorporation.

FIG. 5B shows that fluoxetine-treated animals showed a decreased immobility time, confirming an antidepressant-like effect, and no such effects were observed in irradiated animals (ANOVA, $F_{3,23}$=7.757, n=6 per group, * p<0.05, ** p<0.01).

FIG. 5C shows that significant increases were seen in DG-CA1 relative activity with fluoxetine treatment, but not following irradiation (ANOVA, $F_{3,22}$=3.997, n=5-6 animals per group, * p<0.05). Results corresponded well to observed FST behavior.

FIG. 5D shows that unbiased stereological determination of total BrdU+ cells per hippocampus showed increased numbers of new cells by weeklong fluoxetine treatment (20 mg/kg/day) and decreased by 20 Gy irradiation (ANOVA, $F_{3,24}$=48.92, n=4-8 animals per group,  p<0.01, * p<0.001). BrdU (50 mg/kg/day) was administered concurrently with fluoxetine or vehicle.

FIG. 5E shows phenotyping of BrdU+ cells, determined by scaling the total number of BrdU+ cells (from 5D) by the fraction that expresses each fate-specific marker, revealed that fluoxetine treatment specifically increased the total number of newborn neurons (BrdU+/NeuN+) in the DG (student's t-test, p<0.05, n=6 animals per condition).

FIG. 5F shows immature neuronal marker doublecortin (Dcx) staining was unaffected by fluoxetine, but was abolished by irradiation (ANOVA, $F_{3,24}$=94.44, n=4-8 animals per group, *** p<0.001).

FIG. 5G shows representative confocal images of the DG labeled for BrdU, the mature neuronal marker NeuN, and the astrocytic marker GFAP. Arrowheads indicate BrdU+ cells.

Figure 6:
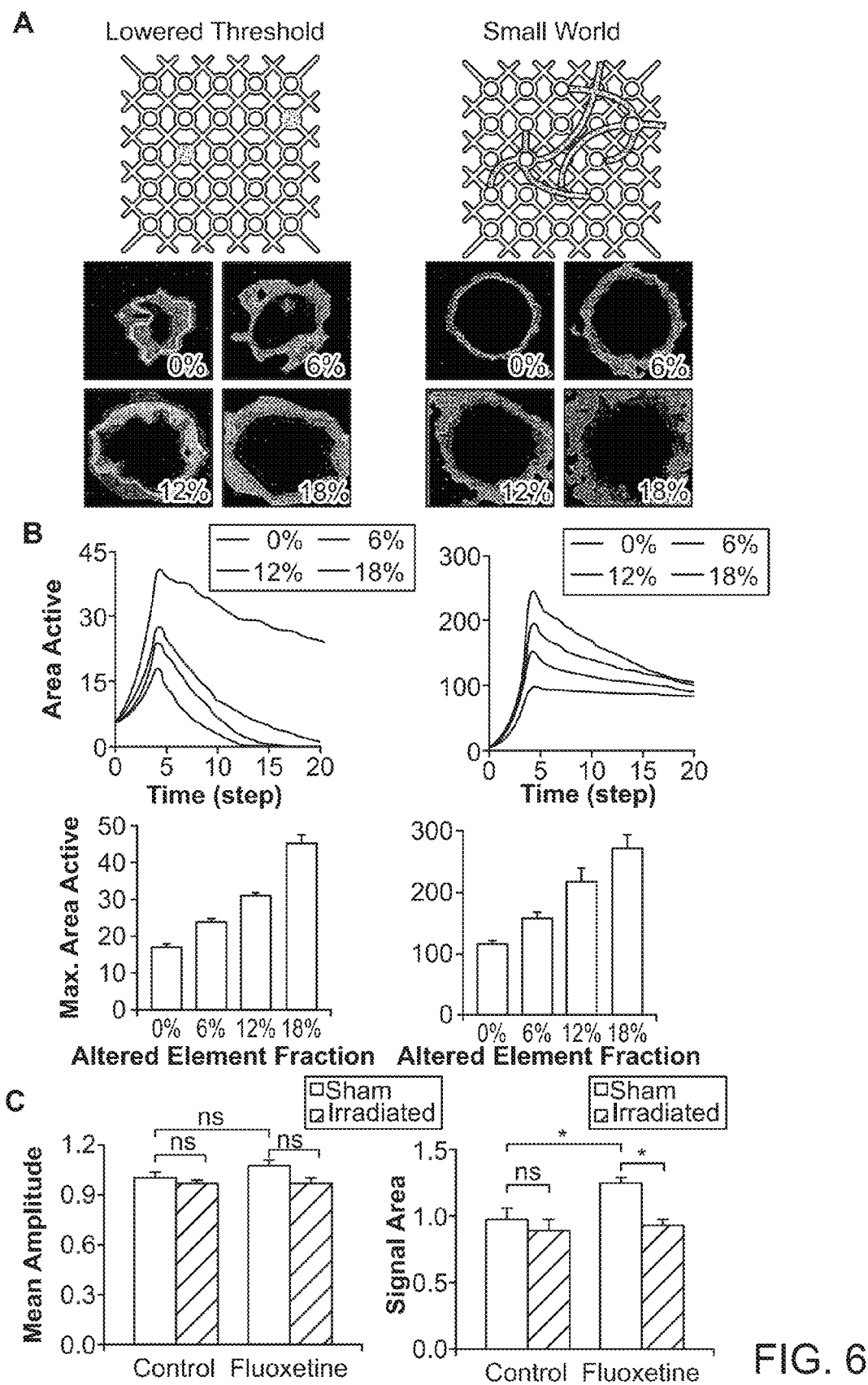
FIG. 6A shows a network model and resulting simulations, consistent with an example embodiment of the present invention.
FIG. 6B shows results from network model and simulations, consistent with an example embodiment of the present invention.
FIG. 6C shows data useful for assessing the experimental effects of neurogenesis on the spread of activity in DG, consistent with an example embodiment of the present invention.

FIG. 6 shows mechanisms by which small numbers of network elements can globally modulate network activity.

FIG. 6A Top: In this simple network model, a small fraction of excitable elements were endowed with either a "lower threshold" response to incoming activity (left), or implemented with longer-range connections (right) creating a "small world" network. Presented are results from simulations on networks with 0%, 6%, 12%, and 18% altered elements. Bottom: Images representing activity increasing with the indicated fraction of altered elements (averaged over 60 simulations), for each network model as above. Images are contour maps of activity averaged across simulations.

FIG. 6B shows quantification of results from both lowered threshold (left) and small world (right) models. Top: Active area (number of active elements) versus simulation time, for each network model. Bottom: Maximum active area increases more steeply than the number of altered elements. Summary graphs showing mean (+SEM) of 60 simulations on networks constructed using the indicated altered-element frequency.

Figure 14:
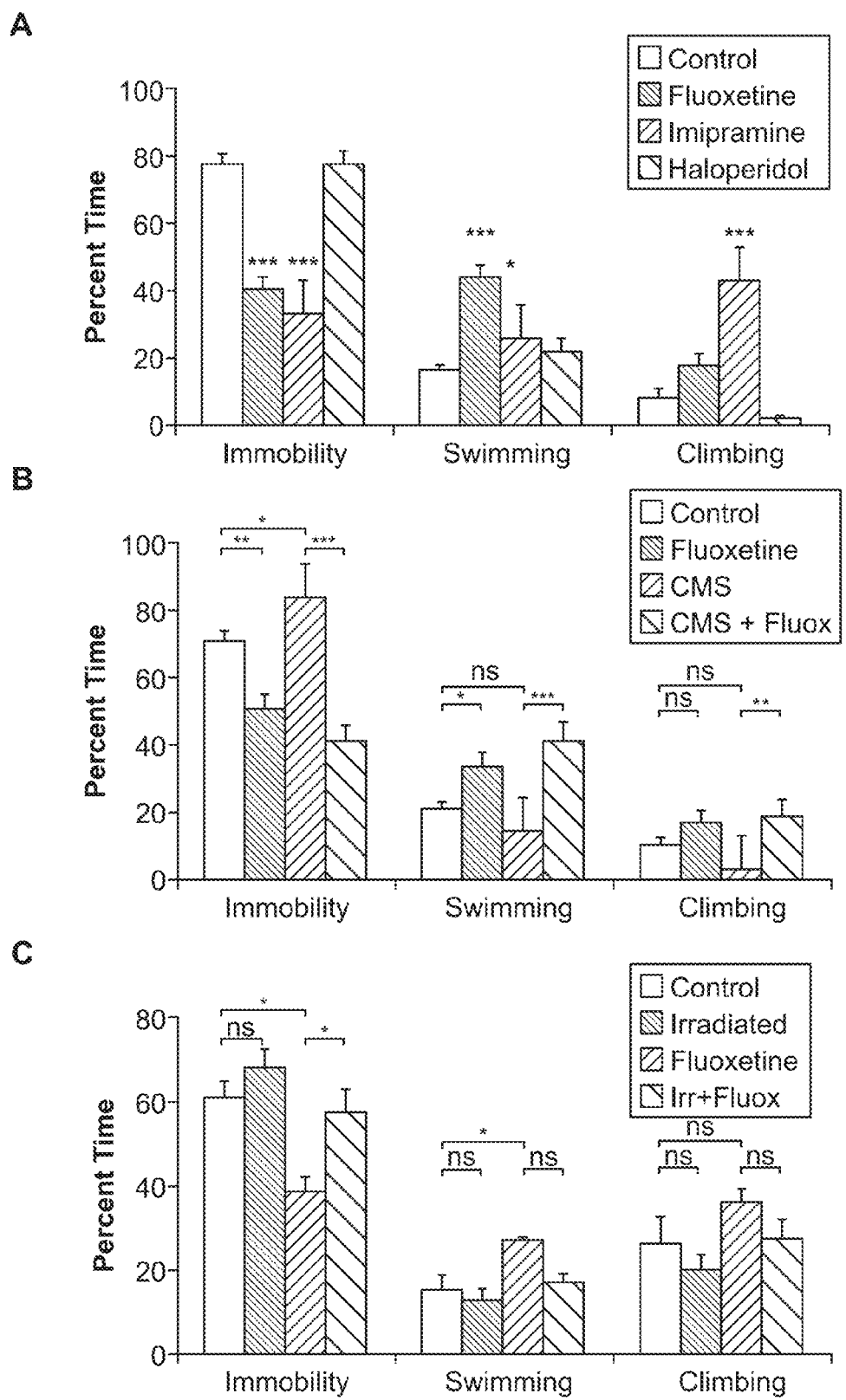
FIG. 14A shows forced-swim test (FST) behaviors presented in response to pharmacological treatment, expressed as a mean percent time and consistent with an example embodiment of the present invention.
FIG. 14B shows FST behaviors presented in response to CMS and fluoxetine, expressed as a mean percent time and consistent with an example embodiment of the present invention.
FIG. 14C shows FST behaviors presented in response to irradiation and fluoxetine, expressed as a mean percent time and consistent with an example embodiment of the present invention.

FIG. 6C shows data useful for assessing the experimental effects of neurogenesis on the spread of activity in DG. Signal area and mean amplitude of recordings in this region were separately analyzed for effects of treatments that modulated neurogenesis. While mean signal amplitude was not modulated by fluoxetine or irradiation treatment (left; ANOVA, $F_{3,179}$=2.390, n=37-60 evoked slice responses per group), the active network area was modulated similarly to the total activity measure (right, ANOVA, $F_{3,180}$=5.502, n=37-60 evoked slice responses per group, * p<0.05; FIG. 14C). All data was normalized by control mean.

Figure 10A:
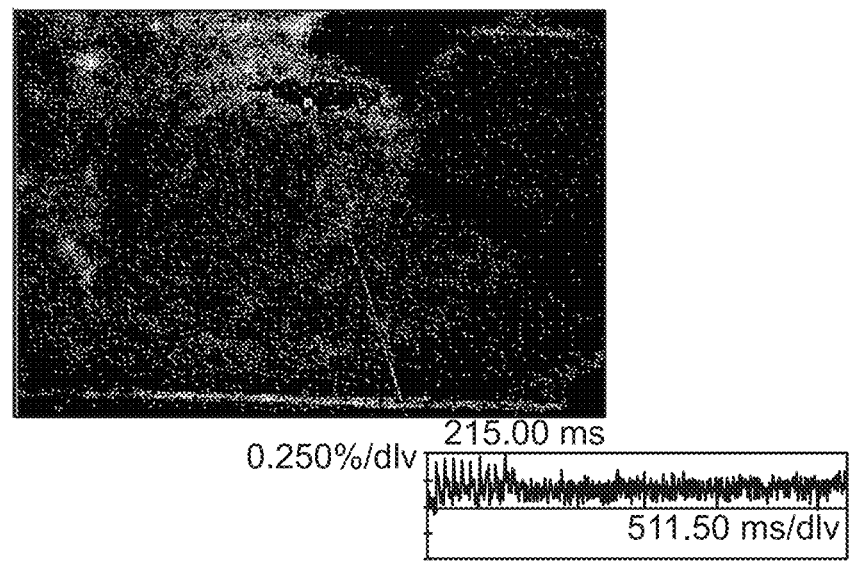
FIG. 10A shows a sample VSDI frame and trace, processed consistent with an example embodiment of the present invention.
Figure 10B:
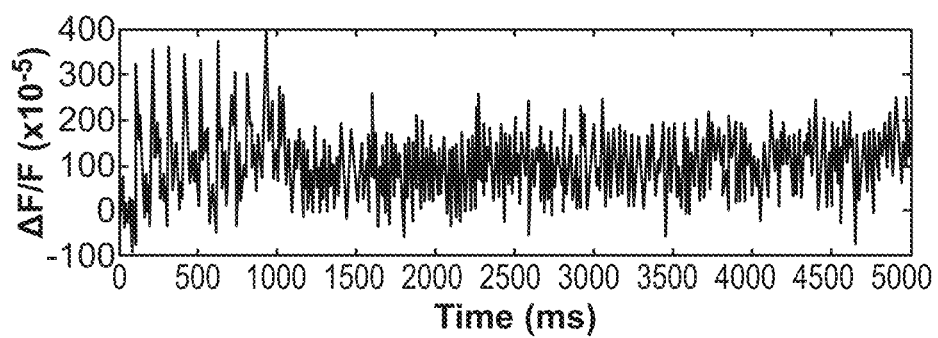
FIG. 10B shows the trace indicated in FIG. 10A, imported into MATLAB, consistent with an example embodiment of the present invention.
Figure 10C:
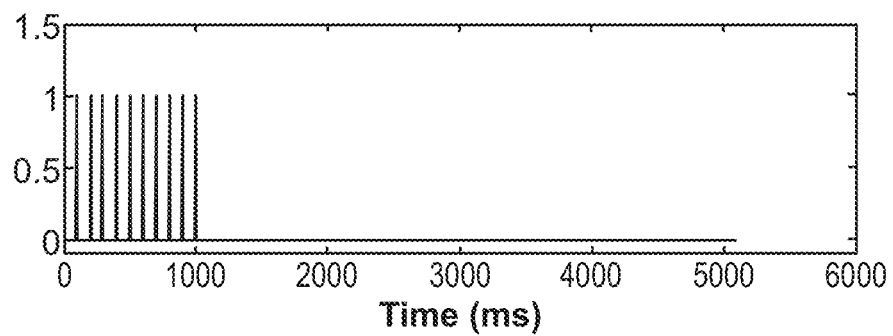
FIG. 10C shows the 10 Hz stimulus profile used during acquisition; consistent with an example embodiment of the present invention.

FIG. 10A shows a screenshot taken from BV Analyzer (Brainvision, RIKEN, Japan; the acquisition program used during imaging) showing a sample VSDI frame and trace, processed consistent with an example embodiment of the present invention. FIG. 10B shows the trace indicated in FIG. 10A, imported into MATLAB. FIG. 10C shows the Hz stimulus profile used during this acquisition.

Figure 11A:
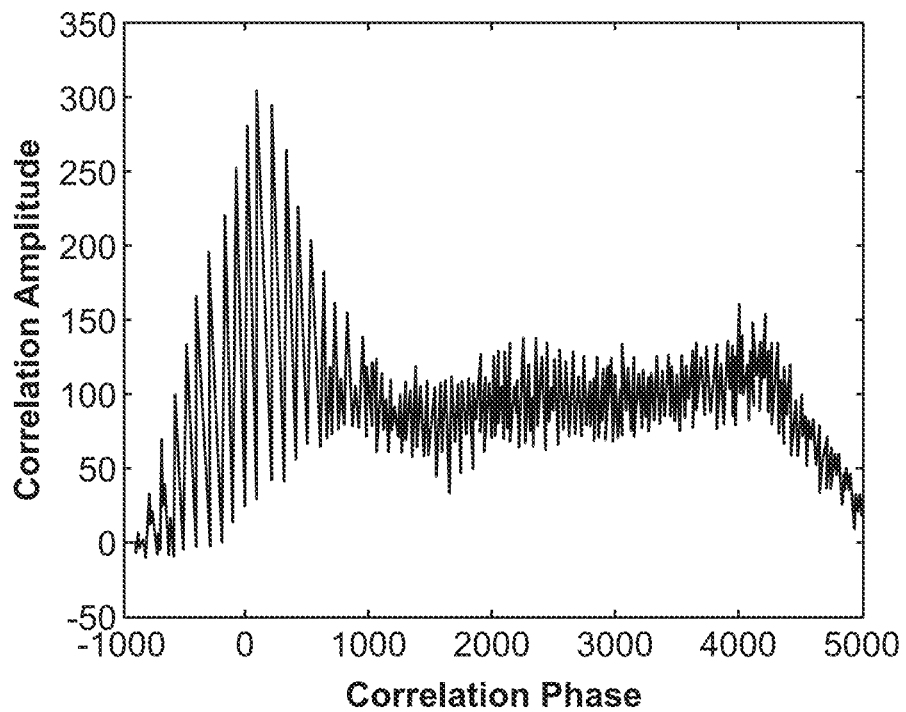
FIG. 11A shows cross-correlogram for a single pixel produced by cross-correlating the stimulus profile against the pixel response, consistent with an example embodiment of the present invention.
Figure 11B:
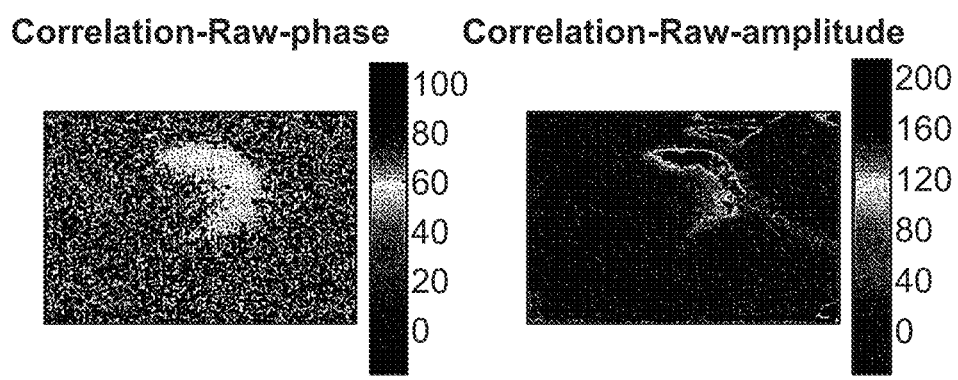
FIG. 11B shows Plot of maximal correlation amplitude and phase of maximal amplitude for each pixel, consistent with an example embodiment of the present invention.
Figure 12A:
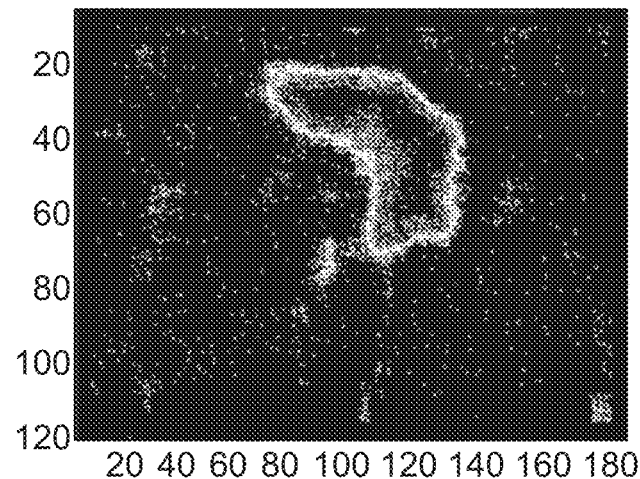
FIG. 12A shows the result of plotting a calculation of standard deviation of phases in the local surrounding area, consistent with an example embodiment of the present invention.

FIG. 11A shows cross-comelogram for a single pixel produced by cross-correlating the stimulus profile against the pixel response, consistent with an example embodiment of the present invention;

FIG. 11B shows a plot of maximal correlation amplitude (right) and phase of maximal amplitude (left) for each pixel. Correlation amplitude units are arbitrary and phase has units of ms, with arbitrary zero point FIG. 12A shows the result of plotting a calculation of standard deviation of phases in the local surrounding area.

Figure 12B:
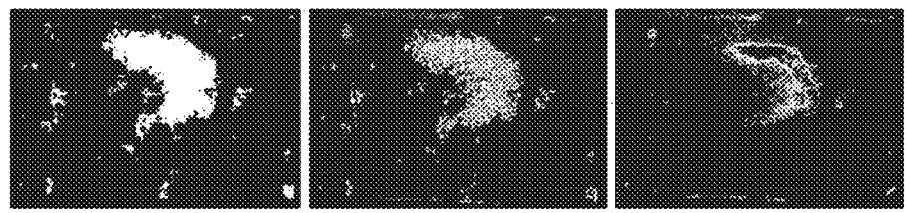
FIG. 12B shows an initial, computationally extracted region of interest, prior to smoothing and manual cropping, and also these pixels overlaid on the phase and amplitude plots of FIG. 10B, consistent with an example embodiment of the present invention.

FIG. 12B shows an initial, computationally extracted region of interest, prior to smoothing and manual cropping, and also these pixels overlaid on the phase (middle) and amplitude (right) plots of FIG. 10B.

Figure 12C:
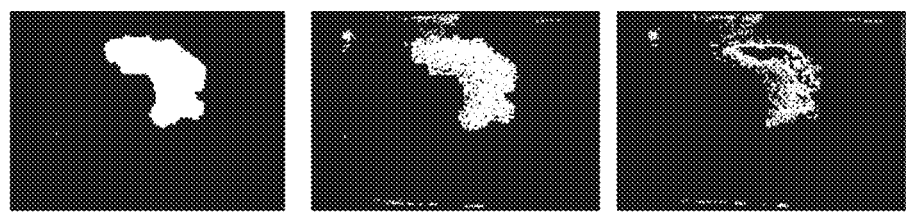
FIG. 12C shows resulting images after morphological smoothing and manual cropping, and also the result overlaid with the phase and amplitude plots of FIG. 10B, consistent with an example embodiment of the present invention.

FIG. 12C shows resulting images after morphological smoothing and manual cropping, and also the result overlaid with the phase (middle) and amplitude (right) plots of FIG. 10B.

FIG. 13A shows selective and specific effects of fluoxetine and hippocampal physiology assessed by immunohistochemistry. Irradiation effects on inflammatory cells were first assessed by immohistochemistry. Shown are images of labeled total microglia (CD11b) and activated microglia (CD68) in sham and irradiated brains. Parallel immunohistochemistry for T cells, B cells, and neutrophils had revealed no cells from these populations in the brain tissue in either control or irradiated conditions. Top row: Total CD11b population comparing typical sham and irradiated brains; expected low levels of microglia are present in both conditions. Middle row: Rare CD68-positive cells were seen in the dentate gyrus of both sham and irradiated brains, with an observable increase in the irradiated brains, as expected since the microglial response is a major mechanism by which neurogenesis is suppressed with irradiation. Bottom row: No CD68-positive cells were observed in the cortex in either condition.

FIG. 13B shows close-up images of CD68-positive activated microglia in sham (top) and irradiated (bottom) hippocampi.

FIG. 13C shows that despite the requisite increase in activated microglia, no effect of irradiation on hippocampal physiology was observed in the non-fluoxetine-treated animals. DG VSDI revealed a significantly increased response in fluoxetine treated animals, while irradiated animals showed no fluoxetine-induced differences corresponding to the lack of new neurons (ANOVA, $F_{3,234}$=7.105, ** $p<0.01$).

FIG. 13D further supports the specificity of irradiation effects to newborn neuron production in DG. CA1 VSDI revealed a significantly decreased response in fluoxetine treated animals that was notably unaffected by irradiation (ANOVA, $F_{3,278}$=4.357, * $p<0.05$). All data was normalized by control means. The lack of irradiation effects in any control behavioral or physiological assay confirms the specificity of this irradiation protocol for ablating hippocampal neurogenesis under these conditions. Additionally, the data reveal two effects of fluoxetine on the hippocampus, a neurogenesis dependent increase of DG activity and a neurogenesis-independent decrease of CA1 activity.

FIG. 14A shows FST behaviors presented in response to pharmacological treatment, expressed as a mean percent time and consistent with an example embodiment of the present invention. Fluoxetine- and imipramine-treated animals show decreased immobility times, and associated increases in swimming and climbing, respectively, confirming an antidepressant effect. No such effects were observed in haloperidol-treated animals (ANOVA, $F_{3,22}$=29.46 (mobility), $F_{3,22}$=16.56 (swimming), $F_{3,22}$=18.64 (climbing), *** $p<0.001$, n=5-6 animals per group).

FIG. 14B shows FST behaviors presented in response to CMS and fluoxetine, expressed as a mean percent time and consistent with an example embodiment of the present invention. CMS-treated animals displayed significantly increased immobility time relative to controls, and fluoxetine treatment decreased immobility in both control and CMS groups. Fluoxetine and CMS+fluoxetine-treated animals showed the associated increases in mobility behaviors (swimming and climbing; ANOVA, $F_{3,34}$=19.24 (immobility), $F_{3,34}$=9.964 (swimming), $F_{3,34}$=5.675 (climbing), * $p<0.05$, $p<0.01$, * $p<0.001$, n=8-12 animals per group).

FIG. 14C shows FST behaviors presented in response to irradiation and fluoxetine, expressed as a mean percent time and consistent with an example embodiment of the present invention. Fluoxetine animals showed decreases in immobility time and increases in swimming, confirming an antidepressant effect, and no such effects were observed in irradiated animals (ANOVA, $F_{3,23}$=7.757 (immobility), $F_{3,23}$, =5.904 (swimming), $F_{3,23}$=1.722 (climbing); * $p<0.05$,** $p<0.01$, n=6 animals per group).

VSDI with a digital camera system optimized for high speed, sensitivity, and resolution was used to observe the activity of intact networks within acute horizontal slices prepared from the ventral hippocampus of adult, female rats (FIG. 1A). Slices were bath loaded with the fast-response voltage-sensitive dye di-4-ANEPPS. After loading, slices were stimulated with standardized electrical pulse trains and activity was recorded with a 5 ms frame rate and 25 um spatial resolution. The signals produced reflected total local network activity and were initiated by excitatory transmission since the AMPA receptor blocker NBQX (10 μM) nearly abolished the signal (FIG. 1B). Concurrent application of the NMDA receptor blocker D-AP5 (25 μM) extinguished the signal as expected. To extract reliable quantitative features of the network response from the high-speed VSDI data, cross-correlation analysis was employed to take advantage of the fact that the evoked responses occur with a uniform fast time course and delay following stimulation and that reverberatory oscillations or changes in response phase were never observed under these conditions (FIGS. 1C, 1D, 10 and 11). This cross-correlation analysis generated two plots, one corresponding to the maximal response amplitude of each pixel (FIG. 1D, top right, FIG. 11B, right), and the other corresponding to the time at which this maximal amplitude occurred ("phase," FIG. 1D, top left, FIG. 11B, left). Phase values were consistent in the regions responding to stimulation, which were isolated computationally for further analysis (FIG. 1D, bottom, FIG. 12). The area of this region of interest and the mean amplitude of pixels in the region were then computed, and local network response ("total activity") was calculated as the mean signal amplitude multiplied by the area of the region of interest. This measure was linear with the applied stimulus current, making it a quantitative and reliable indicator of network activity across animals (FIG. 2B).

Thus, the signal quality, consistency, and linear response of the data showed the usefulness of this high-speed VSDI technology for quantifying abnormalities of intact network dynamics in CNS disease.

To explore hippocampal network activity changes induced in a depression model, a 7-week chronic mild stress (CMS) paradigm was used to elicit an ethologically relevant, depressed-like state in adult, female rats (FIG. 2A, left). Behavioral responses were measured with the modified Porsolt forced swim test (FST), the most widely used animal test predictive of depressed-like states and antidepressant responses. A model of chronic antidepressant treatment was employed by using a 2-week dosing paradigm of fluoxetine, an SSRI antidepressant, or imipramine, a tricyclic antidepressant (FIG. 2A, right). Haloperidol, a typical antipsychotic, was separately administered to determine the specificity of any observed effects to antidepressant treatment. In each drug dosing protocol, a 48-hour delay was incorporated following the last dose to permit behavioral testing in a drug-free state. Experimenters were always blinded to treatment groups. CMS-treated animals spent significantly more time immobile over a 5-minute FST compared to controls, indicating robust induction of a depressed-like state (FIG. 2A, left). Moreover, animals treated with either of the antidepressants showed significantly decreased immobility on the FST, and this effect was absent in animals treated with the antipsychotic haloperidol (FIG. 2A, right).

To determine the network activity changes associated with these induced depression-related behavioral phenotypes, acute hippocampal slices were generated from the same animals for high-speed VSDI. Both the DG and CA1 networks were specifically probed for the reasons described above, anticipating that there would likely be different effects in each local network that might nonetheless each be linked to the behavioral phenotype. For both of these local networks, it was found that the total activity measure is a reliable and quantitative indicator of evoked network activity that is linear with the applied stimulus strength across animals (FIG. 2B). In these and all experiments, the experimenters were always blinded to treatment groups. Strikingly, DG activity was significantly reduced in acute slices from CMS-treated animals (FIG. 2C), while CA1 activity was significantly increased in slices from these animals (FIG. 2D). The activity of the DG relative to that of CA1 has consistently provided a reliable predictor of depression-related behavioral phenotypes (FIG. 2E) that was robust to experimental variation and allowed for quantitative comparisons between individual animals.

The CA1 aspect of this pattern is compatible with previous work linking depression to elevated driving of pathways emerging from the hippocampus, and the DG aspect is consistent with data linking depression to reduced intrahippocampal formation activity. Together this data introduces the concept of an activity mismatch between early associative and late output stages in hippocampal processing. To validate this novel measure, the network-level responses were probed in slices from the antidepressant (fluoxetine, imipramine) or typical antipsychotic (haloperidol) treated animals. Precisely the opposite pattern of network activity was found in antidepressant-treated animals, which showed increased activity in DG (FIG. 2F) and reduced activity in CA1 (FIG. 2G). These effects were specific to the known mood-modulating agents, as the typical antipsychotic haloperidol showed no effect on either hippocampal network (FIG. 2F, 2G). Furthermore, the relative activity of dentate to CA1 (FIG. 2H) continued to provide the most reliable indicator of the behavioral phenotype on an animal-to-animal basis ($r^2=0.5251$, $p<10^{-6}$, pooled across CMS and antidepressant treatment groups).

To assess the generality of the results over conditions that model the clinical use of antidepressants to treat depressed states, animals were exposed to CMS for five weeks to induce a depressed-like state and then administered fluoxetine chronically during the last two weeks of the protocol to reverse the effects of CMS (FIG. 3A). Like the previous antidepressant paradigm, a 48 hour delay period was incorporated between the last fluoxetine dose and the behavioral endpoint to enable testing in a drug free state, and both behavioral and physiological experiments were conducted blind to treatment condition. Behavioral results confirmed the induction of a depressed-like state in CMS-treated animals, and also the efficacy of fluoxetine in reversing the behavioral effects of CMS (FIG. 3A). Moreover, high-speed VSDI data showed that the relative activity between DG and CA1 substantially accounted for these group differences (FIG. 3B), and remarkably, on an individual animal basis, this measure regressed linearly with the bidirectional modulated FST scores and explained over half of the behavioral variation (FIG. 3C). All four independent groups lie along the same tightly correlated line, which would not be expected with random variation within the groups and strongly supports the link between the high-speed physiological metric and FST performance ($r^2=0.5545$, $p<10^{-6}$ in this single experiment). Given the large overlap in both FST and VSDI scores of these groups and the sampling of data points across the full range of both these axes, this circuit dynamics measure substantially accounts for movement along the axis representing affective behavior.

In the same experiment, open field tests (OFT) were also conducted to measure anxiety-related behavior. The relationship between this anxiety measure and network dynamics responses was investigated in order to determine the specificity of the identified network phenotype for the depressed-like state measurement of FST performance (FIG. 3D, 3E, 3F). In OFT, there were no significant differences among the groups in the percent of time the animals spent in the center of the field (FIG. 3D), indicating that the behavioral manipulations were specific for modulating correlates of the effects. Additionally, no effects were seen on the total distance traveled by the animals (FIG. 3E), indicating no confounding effects of the treatments on motility of the animals. This data also indicates that the DG-CA1 relative activity is specific for relating information on correlates of mood as there was no correlation between this physiological metric and the OFT scores (FIG. 3F; $r^2=0.0306$, $p>0.4$).

Next changes in neurogenesis associated with these bidirectional changes in behavior and network activity were probed for, to determine if the network dynamics metric depends chiefly on a single biological mechanism or instead retains its validity across fundamentally different mechanisms that may underlie CMS and antidepressant responses. Neurogenesis appears to be strongly linked to antidepressant effects on the novelty-suppressed feeding task, but has not been clearly implicated in depression-related behavioral measures like the FST or in depression induction involving chronic mild stress. However, acute and severe stress can inhibit neurogenesis, suggesting that altered neurogenesis in some settings could contribute to the etiology of depression. To directly investigate whether the network and behavioral effects of both CMS and antidepressant treatment could depend in part on a common underlying neurogenesis mechanism, bromodeoxyuridine (BrdU) was administered to label dividing cells during the last week of treatment in the experiment described in connection with FIG. 3, and blinded immunohistological counts from the hippocampus contralateral to that used for VSDI were conducted with unbiased stereology procedures, to determine the total number of newborn cells (FIG. 4A, 4C). For this analysis the hippocampal formation was divided into two components, dorsal and ventral. The ventral hippocampus is thought to be more involved in mood regulation. Thus, the acute slice VSDI experiments were conducted in ventral hippocampus. In accord with previous observations, fluoxetine administration robustly increased the newborn cell density in the ventral hippocampus, both in the presence and absence of CMS (control: 1.75 cells/mm$^3$; CMS: 1.68 cells/mm$^3$; fluoxetine: 2.47 cells/mm$^3$; CMS+fluoxetine: 2.38 cells/mm$^3$; FIG. 4A); no such effects were observed in the dorsal hippocampus (control: 3.21 cells/mm$^3$; CMS: 3.09 cells/ mm$^3$; fluoxetine: 3.03 cells/mm$^3$; CMS+fluoxetine: 3.41 cells/mm$^3$; p>0.05 for all comparisons). Interestingly, CMS did not significantly alter newborn cell density (FIG. 4A), in either the dorsal or ventral hippocampus, suggesting that altered neurogenesis is not present in this chronic mild stress protocol and therefore may be very unlikely to mediate either the observed depression-like behavior or the network-dynamics response of CMS.

To definitively demonstrate changes or lack thereof in neurogenesis, the BrdU+ cells were phenotyped using the mature neuronal marker NeuN and the immature neuronal marker Doublecortin (Dcx; FIGS. 4B, 4C). This analysis verified that fluoxetine treatment specifically increased the density of NeuN and Dcx-positive cells in the ventral BrdU+ population, and thus neurogenesis, while the CMS protocol did not alter the fraction of BrdU-positive cells expressing neuronal markers, confirming the lack of effect of this CMS protocol on neurogenesis. Neurogenesis changes might still be causative in some depressed states; this experiment, carried out in the same animals from the experiment in FIG. 3, which demonstrated robust effects of CMS on behavior and network dynamics, indicates that depression-related interventions can be linked to a final common pathway of altered high-speed network dynamics even if initiated by fundamentally different mechanisms.

Figure 13:
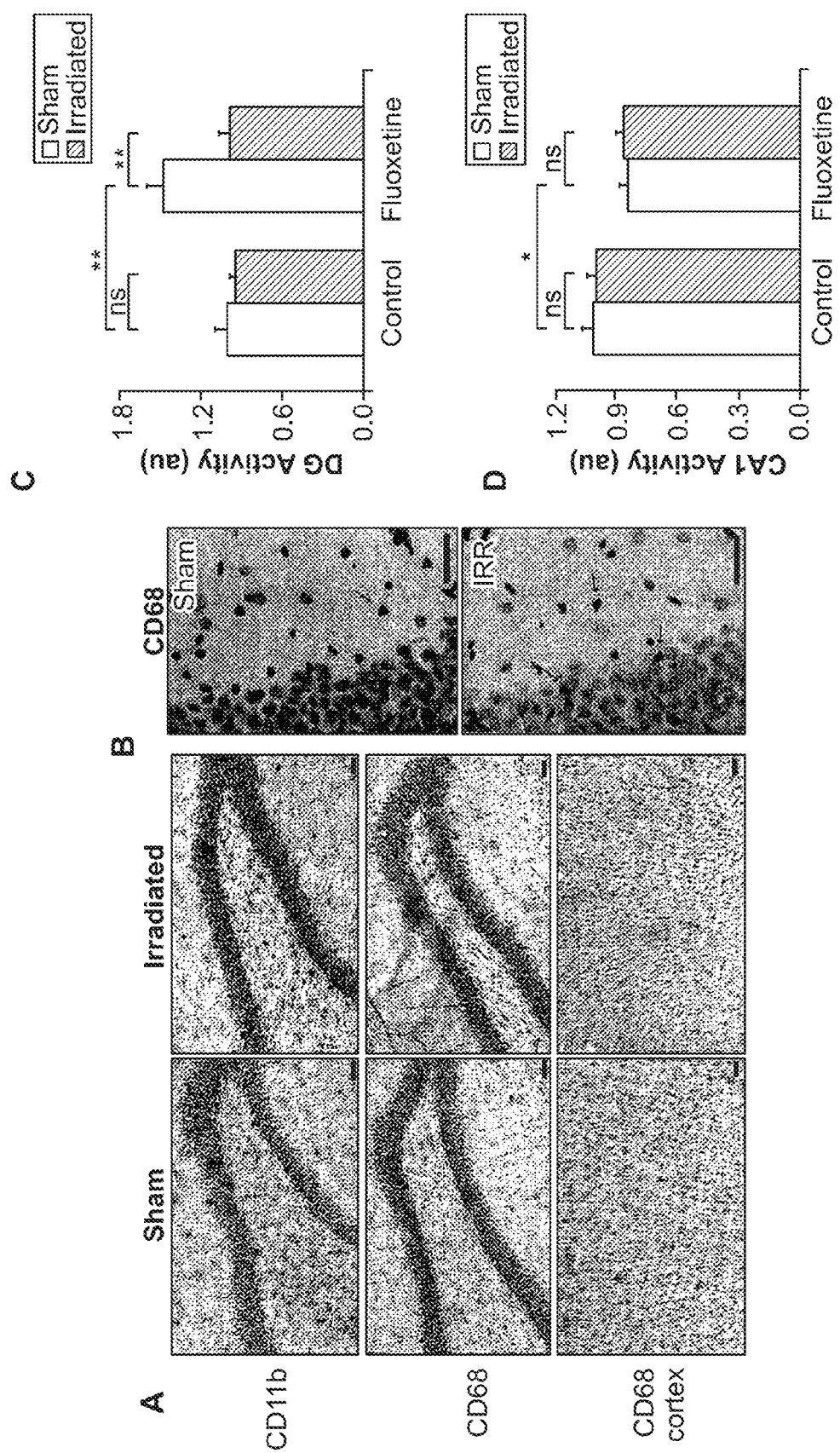
FIG. 13A shows selective and specific effects of fluoxetine and hippocampal physiology assessed by immunohistochemistry, consistent with an example embodiment of the present invention.
FIG. 13B shows close-up images of CD68-positive activated microglia in sham and irradiated hippocampi, consistent with an example embodiment of the present invention.
FIG. 13C the effect of irradiation on hippocampal physiology observed in the non-fluoxetine-treated animals, consistent with an example embodiment of the present invention.
FIG. 13D shows the specificity of irradiation effects to newborn neuron production in DG, consistent with an example embodiment of the present invention.

To further probe the contribution of neurogenesis to the depression-related behavioral and physiological effects of antidepressant treatment, a novel protocol was developed to isolate long-term effects of a temporally defined cohort of fluoxetine-induced newborn neurons. This paradigm incorporates one week of chronic fluoxetine treatment to trigger a burst of neurogenesis, followed by a three week delay period to permit both behavioral testing in a drug-free state and functional integration of neurons born during antidepressant administration (the newborn-neuron specific antidepressant protocol, NNS; FIG. 5A). To control for non-neurogenesis-related effects of antidepressant treatment, in some experimental groups hippocampal neurogenesis was ablated via irradiation (10 Gy/day or sham treatment over two days) one month prior to drug exposure; control experiments resolved no physiological effects of irradiation alone on excitability/network dynamics or behavior on the timescale of these experiments (FIG. 13). Under the NNS protocol, fluoxetine still significantly reduced immobility in the FST (FIG. 5B). This effect was quenched by irradiation, suggesting that hippocampal neurogenesis can be required for depression-related effects of fluoxetine (FIG. 5B). Correspondingly, high-speed VSDI data from the same animals demonstrated that the NNS protocol also increased the activity of DG relative to that of CA1, and that this effect relied similarly on hippocampal neurogenesis (FIG. 5C). Notably, the increased DG activity in response to fluoxetine treatment was significantly dependent on neurogenesis while the decreased CA1 activity was neurogenesis-independent (FIG. 5C); this result would be expected since CA1 does not undergo neurogenesis, providing another control for the specificity of the irradiation treatment under these conditions (FIG. 13).

To quantify effects of the NNS antidepressant treatment on the number of newborn cells and to confirm the selective reduction of hippocampal neurogenesis by irradiation, BrdU was injected during the week of drug treatment and conducted stereological counts as described above. NNS-fluoxetine treatment increased the BrdUi cell density as expected, and irradiation considerably reduced the BrdU+ population (FIGS. 5D, 5G). Phenotyping the BrdUi cells with NeuN and the glial marker GFAP confirmed the selective increase in neurogenesis by the NNS-fluoxetine treatment (FIG. 5E). Additionally, to assess the neurogenic environment at the time of physiological analysis, the immature neuronal marker doublecortin (Dcx) was employed. NNS-fluoxetine treatment did not affect the number of Dcx+ cells, while irradiation eliminated Dcx+ cells (FIG. 5F). Since Dcx is only expressed for approximately 2 weeks after last mitosis in newborn neurons, these data confirmed the permanent effect of irradiation and the transient effect of NNS antidepressant treatment.

These results suggest that while neurogenesis can be important in eliciting behavioral and physiological effects of an antidepressant, it does not follow that changes in neurogenesis necessarily play a significant role in the etiology of the depressed state.

Behaviorally effective CMS treatment did not decrease neurogenesis and ablation of hippocampal neurogenesis in control animals did not induce a depressed-like state (FIGS. 4, 5B). Together, these findings support prior work implicating neurogenesis in some behavioral tests modulated by antidepressants, but indicate that the rate of neurogenesis does not by itself reliably serve as a phenotype tracking behavioral performance, in contrast to hippocampal network dynamics. The data demonstrate that induction of a depressed-like state and antidepressant treatment can share a common link to the network dynamics phenotype, without requiring a common etiological relationship.

Although it has been shown that hippocampal neurogenesis has an impact of antidepressant treatment on the DG network dynamics, it is not immediately obvious how a modest increase in neurogenesis could affect global network activity, especially with estimates that newborn neurons normally comprise only several percent of the DG population. To assess the ability of neurogenesis to implement changes in physiological properties of the whole network, two simple models were generated to study the effect of new neurons on activity propagation (FIGS. 6A, 6B). These models were not constructed to simulate the hippocampus explicitly, but to probe important features of the observations that a small increase in the number of new neurons can affect global flow of activity through networks. In the first model the newborn neurons have a lowered activity threshold, to model the increased excitability of newborn neurons (FIG. 6A, top left). An alternate possibility is that the newborn neurons simply wire differently; to address this possibility, in the second model the new neurons adopt a distinct connectivity pattern relative to the original neurons (FIG. 6A, top right). Existing neurons were connected to only their nearest neighbors while new neurons could generate longer range connections, with lengths chosen from a power law distribution in accord with measured neuronal projection distributions and wiring cost perspectives. Such a network, in which a regular, local connectivity pattern is perturbed by a few elements adopting longer range connections, is known as a "small world" network and has been shown to allow greater network synchronization and activity propagation in more physiologically realistic neural network models.

Dynamics of either model showed that networks with rare new neurons could recruit greatly increased numbers of neurons into activity, compared to networks with no new neurons (FIG. 6A, 6B). Similar results were found in networks in which either afferent or efferent synaptic efficiency was modulated to parallel the enhanced synaptic plasticity associated with new neurons. These results illustrate, over a range of biologically-plausible models, that even small numbers of new elements can modulate global properties of the network. It is important to note that these results also underscore the importance of precise whole network imaging, as slight differences in a small number of neurons can induce non-intuitive, global changes in how information propagates through neural networks without affecting local amplitudes of activity (FIG. 6A). Since voltage sensitive dye imaging can quantify activity changes of whole regions on the millisecond timescale, and with micron spatial resolution, these results support VSDI use as a powerful tool for determining how neural network activity is altered in psychiatric disease.

Since the models demonstrate that adding small numbers of neurons can profoundly affect the spatial extent of activity spread, the experimental data was analyzed regarding features of the experimental VSDI signal itself to determine the contribution of altered signal area to the observed physiological effects of neurogenesis in the DG. The total activity measure derived from the VSDI signal is defined as the product of the area of the active region and the mean amplitude of the signal. No appreciable effect was found of antidepressant-induced neurogenesis on mean signal amplitude (FIG. 5C, left). Instead, the effect of antidepressant treatment on total activity could be explained mostly by an increase in the spatial extent of the spread of activity through the DG, which was blocked by irradiation (FIG. 5C, right). The relative contribution of each signal component to total activity was directly quantified by calculating the mutual information (a measure of how much information one quantity contains about another) between the total activity and either the active network area or mean signal amplitude. With antidepressant treatment, the mutual information between total activity and either area or mean amplitude was noticeably different, with area yielding far more information about total activity ($0.415 \pm 0.051$ bits for area, $0.155 \pm 0.038$ bits for mean amplitude). This analysis demonstrates that the neurogenesis-mediated change in the spatial extent of network activity is a significant contributor to the modulation of hippocampal activity observed in models of antidepressant effect.

A combination of high-speed VSDI, structural analysis, and behavioral testing were employed to probe for depression-linked network abnormalities. First, fast VSD imaging and analysis technology was developed to generate high spatiotemporal-resolution maps of neuronal activity (FIG. 1); this methodology was quantitative and displayed sufficient precision to allow direct linkage of network dynamics to behavior across different treatment groups (FIG. 2). Second, antidepressant and chronic mild stress treatment were demonstrated to give rise to opposite effects on activity in both the DG and CA1 regions of the hippocampal formation, a finding which helps resolve disparate reports in the depression literature (FIG. 2C, 2D, 2F, 2G). It then was shown that the activity of the DG relative to that of CA1 defines a single neurophysiological metric that substantially accounts for mood-correlated behavioral phenotypes (FIG. 2, 3), and is specific for antidepressant treatment medications (FIG. 2) and depression-related behaviors (FIG. 3D, 3E, 3F). On an individual animal basis this measure of hippocampal formation activity regresses linearly with behavioral scores and accounts for over half of the behavioral variation across groups (FIG. 3C), despite fundamentally distinct mechanisms of action of antidepressant treatment and depression-induction protocols (only the former requiring a change in neurogenesis; FIG. 4, 5). This network-level analysis allows for quantitative detection and mechanistic investigation at the relevant spatial and temporal scales in models of psychiatric disease. As substantial changes in network properties were generated by changes in only a small number of cells, and were reflected at the network-level in terms of activity spread rather than amplitude (FIG. 6), it would have been virtually impossible to detect these changes with typical field recording or patch clamp methods. This underscores the unique importance of VSDI in seeking network-level underpinnings of psychiatric disease.

It is important to consider how known etiologies of, and treatments for, major depression are likely to modulate the DG-CA1 relative activity. Considering etiology first, depression-like behavior can be induced without reducing the rate of neurogenesis (FIG. 4), but stress and stress hormones can give rise to existing cell loss in the DG with reduced dendritic arborization, and can also give rise to hyperexcitable CA1 neurons, consistent with the findings on both local networks.

Furthermore, it is certainly possible that acute and severe stress, which can create vulnerability to depression, could reduce new neuron production in human beings as in animals and impair circuit plasticity. Regarding treatments, since insertion of new neurons into the DG appears to be sufficient to drive relevant network-dynamics changes, these data could account in part for the therapeutic effects of the large number of antidepressant treatments known to increase neurogenesis in animal models, including SSRI's, TCAs, electroconvulsive therapy, lithium, environmental enrichment, and exercise. While it is not formally known if the antidepressant-induced newborn neurons in the DG are excitatory or inhibitory themselves or which cell types their axons target, addition of these neurons to the circuit appears to increase total evoked DG network activity (FIGS. 4, 5). Moreover, not only neuron production per se, but also antidepressant-induced increases in neural plasticity and neuron survival could also give rise to the same network dynamics effect, particularly if conditions in the models are satisfied (e.g., the affected neurons are more excitable or couple well to long-range excitatory networks, such as the recurrent hilar mossy cell pathway (FIG. 6).

Some antidepressant treatments clearly do not directly target the hippocampus, such as deep brain stimulation (DBS) which can be targeted to Cg25 or accumbens. However, DBS is known to reduce activity in Cg25 which receives important excitatory projections from the hippocampus, suggesting that subgenual DBS can intervene downstream of an overactive CA1. It had not been known how to unify into a single model the hippocampal atrophy seen in depression with the increase in excitatory driving of cortex from hippocampus associated with clinical depression. These results suggest that the increased activation in the subgenual cingulate during depression could result in part from increased CA1 activity, while reduced intrinsic hippocampal formation function in depression would agree well with the decreased activity of the DG.

In an interesting parallel to the observation that the ratio of DG to CA1 activity in the ventral hippocampal formation predicts mood-related behaviors, dorsal hippocampal memory storage models have described roles for DG and CA1 that involve competitive and comparative interactions in the two local networks. One class of models suggests that CA1 functions in retrieval and transmission to cortex of stored episodic memory, and that the DG gates this retrieval based on contextual information. Other models suggest that the DG, in combination with CA3, generates a predictive signal that is sent to CA1, where this prediction is compared to cortically driven signals representing sensory reality in order to detect unexpected stimuli; the resulting difference signal is then transmitted to cortex. Mood-related hippocampal dysfunction has not been as well modeled but is thought to underlie aspects of the cognitive symptomatology of depression including hopelessness, which can manifest clinically as the inability to foresee or navigate a reasonable and hopeful plan within the context of the patient's environment. Antidepressant treatment that increases the relative activity of the DG to CA1 could drive the hippocampal comparative output in the direction of DG-derived predictive signals, signaling an increase in the ability of the hippocampal formation to model, predict, and plan for the future utilizing contextual information. In contrast, decreasing the activity of DG relative to CA1, as observed in the depressed-like state, would imply impaired recognition and predictive roles of the DG and an inaccurate mismatch signal from CA1 driving cortical structures like Cg25. Whether this signal is interpreted with negative valence (signaling a poor model of the world and therefore hopelessness) or positive valence would depend on concomitant reward pathway activity involving distributed systems in the amygdala, accumbens and mesolimbic dopamine projections.

Identification of this hippocampal neurophysiological endophenotype serves as a starting point in mapping the network-level changes in other brain regions implicated in depression, such as the prefrontal and cingulate cortices, amygdala, basal ganglia, and reward centers. While these other brain regions are undoubtedly involved in depression physiology, the ability of this hippocampal measure to convey information regarding the animal's behavioral state supports the emerging hypothesis that the hippocampus plays a primary role in mood regulation, in addition to its accepted role in learning and memory. High-speed, whole network analysis with VSDI is clearly indicated to probe changes in other implicated brain regions, in models of depression and other neuropsychiatric disorders. Using the techniques and methods discussed herein it should be apparent that more detailed models of altered activity flow are possible and that this methodology can be extended to other depression models and treatment paradigms. This putative endophenotype is contemplated for use in screening for treatments that specifically and similarly modulate hippocampal dynamics. Depression and antidepressant-induced changes to neural circuitry can be monitored using the techniques and systems discussed herein and may be useful for achieving a quantitative understanding of the depressed brain.

Accordingly, the various methods and systems described herein can be used for the treatment of depressed states in patients. In one such instance, the effectiveness of drugs and other treatment techniques can be quantitatively measured and tailored to minimize unwanted side-effects. In another instance, the characteristics of the CA1 and DG in a patient can be used to make diagnosis of the patient's depressed state. Whether implemented in vitro on a neural network of a related specimen or in vivo on the neural network of the same subject, these approaches can be particularly useful for determining which patient treatments would be most effective.

Such a method need not be conducted in slices. For example, using infrared imaging, in which a high-resolution CCD camera is implanted next to the brain structure of interest, the brain circuits of a living organism can be scanned in real time, with areas of interest analyzed in accordance with the presently described method. As infrared tomography (from external to the body) advances in capabilities, it is anticipated that these methods will permit acquisition of data at sufficient temporal and spatial resolution so as to serve within the context of the present invention.

For further details regarding modeling depression through use of various embodiments of the present invention reference can be made to "High-Speed Imaging Reveals Neurophysiological Links to Behavior in an Animal Model of Depression" by Airan et al. (*Science*, Aug. 10, 2007, Vol. 317 pp. 819-823), which is fully incorporated herein by reference.

While the VSDI signals received in embodiments of the invention are robust and reliable, the known low signal to noise ratio can be compensated for using various design and analyses. In one such example, only evoked responses are considered so that stimulus/response cross-correlation analysis can be utilized to take advantage of the known response timing. Additionally, for proper cross-slice and animal comparison, an algorithm is used to automatically and efficiently extract relevant parameters of the signal (region of interest, mean amplitude, etc.) from the data. Peak response amplitude of $-0.1\%$ $\Delta F/F$ was sufficient for proper signal extraction.

The following algorithms provide an example implementation for use in analyzing the VSDI data collected according to the methods and systems described herein. To begin the analysis, the raw VSDI data were imported into a software application, such as MATLAB (Mathworks, Natick, Mass.). The data was represented as an initial reference frame (F), followed by each imaging data frame, which contained differential fluorescence values ($\Delta F$). For each pixel and frame, the $\Delta F/F$ value was calculated. Each temporal frame was then spatially smoothed using a 3×3 pixel digital Gaussian kernel ($\sigma=1$):

$$\frac{1}{16} \times \begin{bmatrix} 1 & 2 & 1 \\ 2 & 4 & 2 \\ 1 & 2 & 1 \end{bmatrix} \quad (1)$$

During imaging, multiple individual sweeps (e.g., four sweeps) are recorded of activity responding to stimulation with each frequency and in each region. Following spatial averaging, these four sweeps were averaged frame by frame, producing one VSDI movie (FIG. 10). Next, each pixel in the movie was treated independently, and a cross-correlation was computed.

$$\phi_{sr}[m] = \sum_{n=-\infty}^{\infty} s[n]r[n+m], \quad (2)$$

Where r[ ] is the pixel's response signal and s[ ] is the stimulation profile used during acquisition (FIG. 11A).

The maximum of the cross-correlation amplitude (max [$\varnothing_{sr}$[m]]), which measures the system's response to stimulation, was then found for each pixel, as well as the delay of this peak (phase=arg[max[$\varnothing_{sr}$[m]]). If there is an arbitrary software delay of the camera system used, the phase values at this stage are arbitrary with respect to the real latency of response to stimulation.

Timing of the response with respect to the stimulus can be calculated later using an absolute reference point inserted by closing a shutter during acquisition prior to stimulation.

To extract the region of interest, it is observed that pixels in this region tended to be clustered and of similar phase to one other (FIG. 11B, left). In contrast, the phase is random and incoherent in regions which might have high correlation amplitude, but in reality correspond to noise or artifacts—compare the dark red regions (non-tissue containing pixels) in FIG. 11B (right) to their corresponding phases (left). To quantify this clustering, for each pixel, the standard deviation (SD) of phase values in the surrounding 7×7 pixel region was computed (FIG. 12A). Region of interest pixels had a lower standard deviation, whereas noise regions generate random phase values and correspondingly higher standard deviation. The phases of the pixels that had the lowest SD (threshold set at SD=32.5 ms in analysis) were calculated as the initial distribution of phases in the region of interest.

To remove outlying values, the upper and lower 25% of the distribution was replaced by a padding (initially plus or minus 25 ms). The pixels with phases in this range were defined to be part of the region of interest. If the number of pixels in this region was too low (less than 3% of the total frame size), this suggested a relatively broad phase range of the true region of interest and the padding was incremented until this number of pixels was above an absolute threshold (3% of the frame size). The resultant pixels formed the initial calculated region of interest (FIG. 12B).

Upon defining this initial region of interest, median filtering with a 3×3 pixel window was completed to remove spurious pixels outside the region of interest, and morphological smoothing (first image-opening by 4 pixels and then image-closing by 6 pixels) was completed to close gaps existing within the region of interest. To remove any pixels outside the region of interest, the resulting pixel maps were manually cropped with the user blinded to treatment group producing the final, extracted region of interest (FIG. 12C).

After extracting the region of interest, the mean correlation amplitude of pixels within this region and the total area of the region of interest (as a percentage of frame size) were then calculated. The mean amplitude multiplied by this area ("total activity") was the final statistic used to measure system response for the voltage sensitive dye imaging data. Even though voltage changes due to glia can be observed with voltage sensitive dyes, the total activity measures reported here likely indicate only neuronal responses to stimulation, as opposed to the slower responses of hippocampal glia that are not appreciably sensitive to AMPA and NMDA block especially given the short latency to peak of the VSDI traces (6.3+/−0.6 ms for 2 Hz stimulations), the lack of summation of responses following 2 Hz stimulation, and the reliance of the signal on AMPA and NMDA transmission (FIG. 1B).

In one embodiment of the present invention, the aforementioned algorithms can be iteratively applied so as generate a large-scale image of general neural activity. This large-scale image can be more informative than less precise methods because the image is derived from precise temporal and spatial data obtained from a number of the relatively small portions of subfields.

Additionally, while asynchrony in the individual responses in principle could yield a modulation of the correlation amplitude relative to the absolute activity in the network, the phase values local to each pixel were tightly correlated and not observably patterned and no consistent effects on phase were noted between the various treatments. These results combined with short latency of the responses indicate that there is not a significant contribution of asynchronous responses to extracellular stimulation in these experiments. Furthermore, given the minimal role of the mean amplitude in modulating total activity (FIG. 6C), it is unlikely that asynchrony in the neuronal responses would significantly bias this statistic. Accordingly, while modulation of the total activity due to this asynchrony can not be ruled out, because of the reduced role of mean in affecting total activity, the lack of variation of the phase information between treatment groups, and the low expected asynchrony in the evoked responses, the contribution of this modulation is likely to be minimal to the observed effects on network activity, which are quantified by total activity. The VSDI signal amplitude represents a population signal similar to that of a field-excitatory-postsynaptic potential (fEPSP) and the total activity measure represents a signal similar to that of a fEPSP integrated spatially across the region of interest and temporally across the peak evoked responses to 10 stimulus pulses.

Aspects of the present invention can be used in combination with a variety of neuron-directed applications, including those which are discussed in the related background articles cited above and listed herewith. For example, for detailed discussion of in vivo VSDI applications, reference may be made to "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstruction" (*The Journal of Neuroscience*, Feb. 15, 2003, 23(3) pp. 1298-1309), which is fully incorporated herein by reference. Another example that is specifically directed to hippocampal CA1 aspects is discussed in the article entitled "Hippocampal CA1 Circuitry Dynamically Gates Direct Cortical Inputs Preferentially at Theta Frequencies" (*The Journal of Neuroscience*, Oct. 19, 2005, 25(42) pp. 9567-9580), which is fully incorporated herein by reference.

Various applications of the invention can be applied to any disease where percolation of activity, excitation, inhibition, or the ratio of excitation to inhibition between two or more cell populations may be usefully addressed with imaging and processing techniques disclosed herein. For example, in Alzheimer's disease, the hippocampus and entorhinal cortex become diseased early. Mild cognitive impairment (MCI) may be a hallmark of this early AD process. Down Syndrome is manifested by a number of neurological abnormalities developed as a result of gene expression from an extra 21st chromosome. Among these are underdeveloped brain structures including the temporal lobe, and a nearly universal propensity for developing Alzheimer's disease. Autism, schizophrenia, bipolar disorder and many other conditions may be studied and improved treatments developed by identifying circuit-level endophenotypes as described in the present application, and using these as a well-circumscribed paradigm in which to target candidate treatments.

Various embodiments of the invention are useful to elucidate the role of one or more elements within a circuit. For example, one aspect involves assessing the interdependency (or independence) of areas of a subfield from the level of activity of areas of the subfield circuit. Quantitative analysis allows interdependencies to be identified and decoded.

Other embodiments of the invention can be used to elucidate the location of the activity of a drug within that circuit. For example, a drug may be added to the neural circuit, and the locations of activity change (relative to activity without the drug) are readout and recorded. These changes can be used to assess both primary sites of action, and downstream effects upon the greater circuit.

Another embodiment of the invention can be used to elucidate the effect of a drug on a given circuit. For example, specifically looking for fast acting/acute acting drugs, such as ketamine, for depression, by bath applying the drugs to find the right acute drug and drug dose that tunes activity in the desired manner in the high-throughput screening setting, thereby identifying drugs that act in days or hours rather than weeks/months Other embodiments can be used to identify endophenotypes that have the high predictive value for a given disorder or to identify target locations for physical interventions including electrical, magnetic stimulation and ultrasound and radiation treatments.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include uses for neurological characteristics other than depression, such as other diseases, disorders and even the study of normal activity. Other such changes include various in vivo imaging implementations. Such modifications and changes do not depart from the true spirit and scope of the present invention, which is set forth in the following claims.

What is claimed is:

1. A method for assessing neural activity of a neural tissue in a neural region having multiple subfields, the method comprising:
    evoking a cellular electrical response in at least one subfield of the neural tissue due to neural activity in the neural region, wherein neuronal cells in the neural region express a light-activated ion channel and/or a light-activated ion pump protein;
    capturing image data of the cellular electrical response at space and time limits of resolution that allow for the differentiation between polarization-based events of two portions of the at least one subfield, wherein each of the two portions comprises a group of neurons; and
    assessing neural activity by correlating space and time information, from the captured data, for the two portions of the at least one subfield.

2. The method of claim 1, wherein evoking an electrical response comprises exogenously affecting the neural region.

3. The method of claim 1, wherein evoking an electrical response comprises stimulating the neural region.

4. The method of claim 1, wherein evoking an electrical response comprises passively monitoring electrical activity occurring in an otherwise unstimulated environment.

5. The method of claim 1, wherein the cellular electrical response is evoked by optical stimulation of the light-activated ion channel and/or the light-activated ion pump protein.

6. A system for assessing neural activity, the system comprising:
    a composition comprising a nucleic acid encoding a light-activated ion channel and/or a light-activated ion pump protein;
    a stimulator configured to evoke a cellular electrical response in at least one subfield of a neural tissue in a neural region having multiple subfields by optically stimulating neuronal cells of the neural region that comprise the nucleic acid and express the light-activated ion channel and/or the light-activated ion pump protein;
    an imager configured to capture image data of the cellular electrical response at space and time limits of resolution that allow for differentiation between polarization-based events of two portions of the at least one subfield, wherein each of the two portions comprises a group of neurons; and
    a processor configured for assessing neural activity, wherein assessing neural activity comprises correlating space and time information, from the captured image data, for the two portions of the at least one subfield to produce correlation results.

7. The system according to claim 6, further comprising a composition for staining the neural tissue, wherein the composition comprises at least one of: a voltage sensitive dye, and a calcium sensitive dye.

8. The system according to claim 6, wherein the correlation results comprise a correlation between a signal strength of a stimulation profile and each pixel in the image data, and wherein the processor is further configured for:
    determining the correlation between the signal strength of the stimulation profile and each pixel in the image data;
    determining a cross-correlation amplitude for each pixel based on the determined correlation;
    determining a cross-correlation phase for each pixel based on the determined correlation;
    identifying areas of interest as a function of a spatial location of each pixel and the determined cross-correlations; and
    limiting pixel variations in the image data that are not in the identified areas of interest.

9. The system according to claim 8, wherein limiting pixel variations in the image data that are not in the identified areas of interest comprises median filtering the image data.

10. The system according to claim 9, wherein the median filtering comprises median filtering with a 3×3 pixel window.

11. The system according to claim 6, wherein the processor is further configured for: assessing target locations for a treatment that includes a physical intervention.

12. The system according to claim 6, further comprising a computer arrangement comprising:
    the processor; and
    a storage medium storing computer-executable data, wherein, when the computer-executable data is executed by the processor, the processor assesses neural activity by correlating space and time information, from the captured data, for the two portions of the at least one subfield.

13. The system according to claim 6, wherein assessing neural activity further comprises comparing the correlation results with and without a treatment for the neural region, wherein the treatment is at least one of: a pharmacological chemical based substance, a nonchemical-based therapeutic treatment, a neural-invasive treatment, a neural-genesis treatment, and a neural-modulation treatment.

14. The system according to claim 6, wherein assessing neural activity further comprises assessing endophenotypes for a predictive value relative to a disorder.

15. The system according to claim 6, wherein assessing neural activity further comprises assessing a role of one or more subfields within a neural circuit.

16. The system according to claim 6, wherein neural activity is assessed relative to a depressed state of the neural region.

17. The system according to claim 6, wherein neural activity is assessed relative to one or more of: Alzheimer's disease, mild cognitive impairment, autism, bipolar disorder, schizophrenia, and Down Syndrome.

18. The system according to claim 6, wherein:
the space limit of resolution is less than a centimeter;
the time limit of resolution is less than 500 milliseconds; and
the polarization-based events involve at least one of: depolarization events and hyperpolarization events.

19. The system according to claim 6, wherein the space limit of resolution is less than about a millimeter.

20. The system according to claim 6, wherein the subfields include dentate gyrus (DG) and CA1 subfields of the hippocampus.

21. The system according to claim 6, wherein the neural region is selected from the group consisting of hypothalamus, frontal cortex, entorhinal cortex, cingulate cortex, mammillary bodies, septum, bed nucleus of stria terminalis, amygdala, and accumbens.

22. The system according to claim 6, wherein the light-activated ion channel and/or the light-activated ion pump protein is at least one of: a channel-rhodopsin (ChR2), and a halorhodopsin (NpHR).

23. The system according to claim 6, wherein the neural tissue is a brain slice.

* * * * *

UNITED STATES PATENT AND TRADEMARK OFFICE
CERTIFICATE OF CORRECTION

PATENT NO. : 9,693,692 B2  Page 1 of 1
APPLICATION NO. : 13/763132
DATED : July 4, 2017
INVENTOR(S) : Deisseroth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1121 days.

Signed and Sealed this
Twenty-fifth Day of September, 2018

Andrei Iancu
*Director of the United States Patent and Trademark Office*